US011097129B2

(12) United States Patent
Sakata et al.

(10) Patent No.: US 11,097,129 B2
(45) Date of Patent: Aug. 24, 2021

(54) OBJECT POSITIONING APPARATUS, OBJECT POSITIONING METHOD, OBJECT POSITIONING PROGRAM, AND RADIATION THERAPY SYSTEM

(71) Applicant: Toshiba Energy Systems & Solutions Corporation, Kawasaki (JP)

(72) Inventors: Yukinobu Sakata, Kawasaki (JP); Yasunori Taguchi, Kawasaki (JP); Ryusuke Hirai, Shinagawa (JP); Keiko Okaya, Setagaya (JP); Shinichiro Mori, Chiba (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 206 days.

(21) Appl. No.: 15/921,183

(22) Filed: Mar. 14, 2018

(65) Prior Publication Data

US 2018/0264288 A1  Sep. 20, 2018

(30) Foreign Application Priority Data

Mar. 16, 2017  (JP) .............................. JP2017-051076

(51) Int. Cl.
| | |
|---|---|
| *A61B 6/03* | (2006.01) |
| *A61N 5/10* | (2006.01) |
| *A61B 6/00* | (2006.01) |
| *G06T 11/00* | (2006.01) |
| *G06T 7/73* | (2017.01) |
| *A61B 6/04* | (2006.01) |

(52) U.S. Cl.
CPC ............ *A61N 5/1049* (2013.01); *A61B 6/035* (2013.01); *A61B 6/4014* (2013.01); *A61B 6/485* (2013.01);
(Continued)

(58) Field of Classification Search
CPC ........... A61B 5/0555; A61B 6/00; A61B 6/02; A61B 6/03; A61B 6/032; A61B 6/035;
(Continued)

(56) References Cited

U.S. PATENT DOCUMENTS

| | | | |
|---|---|---|---|
| 5,975,893 A | 11/1999 | Chishti et al. | |
| 6,470,207 B1* | 10/2002 | Simon ..................... | G06F 19/00 600/426 |

(Continued)

FOREIGN PATENT DOCUMENTS

| | | |
|---|---|---|
| JP | 2009-189461 | 8/2009 |
| JP | 2015-186537 | 10/2015 |

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

An object positioning apparatus comprising: a radiographic image input interface configured to acquire a radiographic image that is generated by causing a fluoroscopic imaging apparatus to image an object and includes a first region and a second region, the first region depicting an index region for positioning of the object, the second region depicting a non-index region other than the index region; and a positioning processor configured to perform the positioning of the object by performing matching processing between a previously generated reference image and the first region that is specified from the radiographic image based on three-dimensional model information of the non-index region.

7 Claims, 17 Drawing Sheets

(52) U.S. Cl.
CPC ............... *A61B 6/487* (2013.01); *G06T 7/75* (2017.01); *G06T 11/005* (2013.01); *A61B 6/04* (2013.01); *A61N 5/1037* (2013.01); *A61N 2005/1061* (2013.01); *A61N 2005/1062* (2013.01); *G06T 2207/10081* (2013.01); *G06T 2207/10121* (2013.01)

(58) Field of Classification Search
CPC ....... A61B 6/04; A61B 6/0407; A61B 6/0421; A61B 6/0414; A61B 6/0428; A61B 6/0435; A61B 6/0442; A61B 6/045; A61B 6/0457; A61B 6/0478; A61B 6/0485; A61B 6/0492; A61B 6/44; A61B 6/54; A61B 6/545; A61B 6/547; A61G 2210/50; A61N 2005/1057; G01N 23/046; H01J 37/20; H01J 2237/20; H01J 2237/2007

See application file for complete search history.

(56) References Cited

U.S. PATENT DOCUMENTS

| | | |
|---|---|---|
| 2011/0176656 A1 | 7/2011 | Kyushima et al. |
| 2013/0345718 A1* | 12/2013 | Crawford ............. A61B 17/025 606/130 |
| 2014/0205167 A1 | 7/2014 | Kleiner |
| 2016/0148401 A1 | 5/2016 | Hirai et al. |
| 2016/0155228 A1* | 6/2016 | Sakata ...................... G06T 7/11 382/132 |
| 2017/0043184 A1 | 2/2017 | Mori et al. |
| 2019/0290363 A1* | 9/2019 | Blau ...................... G06T 7/0014 |

FOREIGN PATENT DOCUMENTS

| | | |
|---|---|---|
| JP | 2016-101358 | 6/2016 |
| TW | 471960 B | 1/2002 |
| TW | I511555 B | 12/2015 |
| TW | I565450 B | 1/2017 |

\* cited by examiner

X-RAY IMAGE (BEFORE REMOVING SPECIFIC REGION)

X-RAY IMAGE (AFTER REMOVING SPECIFIC REGION)

X-RAY IMAGE (BEFORE REMOVING SECOND REGION)

X-RAY IMAGE (AFTER REMOVING SECOND REGION)

X-RAY IMAGE BEFORE IMAGE PROCESSING
(INCLUDING FIRST AND SECOND REGIONS)

PIXEL VALUE X(u, v) ON LINE L

DRR IMAGE OF NON-INDEX REGION (SECOND REGION)

PIXEL VALUE I(u, v) ON LINE L

X-RAY IMAGE AFTER IMAGE PROCESSING (FIRST REGION)

PIXEL VALUE A(u, v) ON LINE L

IMAGE OF SURFACE COMPONENT (FIRST REGION)

PIXEL VALUE T(u, v) ON LINE L AFTER SUBTRACTION

X-RAY IMAGE AFTER IMAGE PROCESSING
(FIRST REGION)

PIXEL VALUE A(u, v) ON LINE L

OBJECT POSITIONING APPARATUS, OBJECT POSITIONING METHOD, OBJECT POSITIONING PROGRAM, AND RADIATION THERAPY SYSTEM

CROSS-REFERENCE TO RELATED APPLICATION

This application is based upon and claims the benefit of priority from Japanese Patent Application No. 2017-051076, filed on Mar. 16, 2017, the entire contents of which are incorporated herein by reference.

FIELD

Embodiments of the present invention relates to an object positioning apparatus, an object positioning method, an object positioning program, and a radiation therapy system.

BACKGROUND

In radiotherapy, a DRR (Digitally Reconstructed Radiograph) image is generated on the basis of a three-dimensional image acquired by using a CT (Computed Tomography) apparatus at the time of treatment planning, and positioning of a patient is executed by performing matching processing between the DRR image and an X-ray image that is obtained by imaging the patient before irradiation of radioactive rays. Here, there is a technique for generating a DRR image in which only the pixel region of the patient is extracted and depicted even when pixel regions depicting unnecessary objects such abed and a medical restraint are included in the three-dimensional image at the time of treatment planning.

[Patent Document 1] Japanese Unexamined Patent Application Publication No. 2016-101358

In the above-described technique, though pixel regions depicting unnecessary objects such as the bed and the medical restraint are removed from the DRR image (i.e., reference image) generated at the time of treatment planning, an X-ray image (i.e., imaged image or radiographic image) before radiation irradiation is in the state of including the unnecessary pixel regions such as the bed and the medical restraint. Such unnecessary pixel regions become obstacles to the positioning of the patient, which causes a problem that it is difficult to perform the positioning of the patient.

In view of the above-described problem, an object of embodiments of the present invention is to provide object positioning technology by which matching accuracy between a radiographic image and a reference image can be improved and positioning of the patient can be facilitated.

DETAILED DESCRIPTION

In one embodiment of the present invention, an object positioning apparatus comprising:

a radiographic image input interface configured to acquire a radiographic image that is generated by causing a fluoroscopic imaging apparatus to image an object and includes a first region and a second region, the first region depicting an index region for positioning of the object, the second region depicting a non-index region other than the index region; and a positioning processor configured to perform the positioning of the object by performing matching processing between a previously generated reference image and the first region that is specified from the radiographic image based on three-dimensional model information of the non-index region.

According to embodiments of the present invention provide object positioning technology by which matching accuracy between a radiographic image and a reference image can be improved and positioning of the patient can be facilitated.

First Embodiment

Hereinafter, embodiments will be described with reference to the accompanying drawings. First, a description will be given of an object positioning apparatus according to of the first embodiment by referring to FIG. 1 to FIG. 15B. The reference sign 1 in FIG. 1 denotes a radiation therapy system used for radiotherapy, in which a lesion area G such as a tumor generated in a body of a patient P is irradiated with radioactive rays R. The radioactive rays R used for treatment include, e.g., X-rays, γ-rays, electron beams, proton beams, neutron beams, and heavy particle beams.

When radiotherapy is performed, the radioactive rays R with sufficient output must be accurately radiated onto the position of the lesion area G (i.e., target area) of the patient (i.e., object) P. Further, it is necessary to suppress exposure dose of normal tissues (i.e., non-target area) in the vicinity of the lesion area G. For this reason, in the present embodiment, the positioning of the patient P is executed by performing the matching processing between the image of the patient P acquired at the time of treatment planning and the image of the patient P imaged at the time of radiation irradiation, and then the radioactive rays R are radiated.

Figure 1:
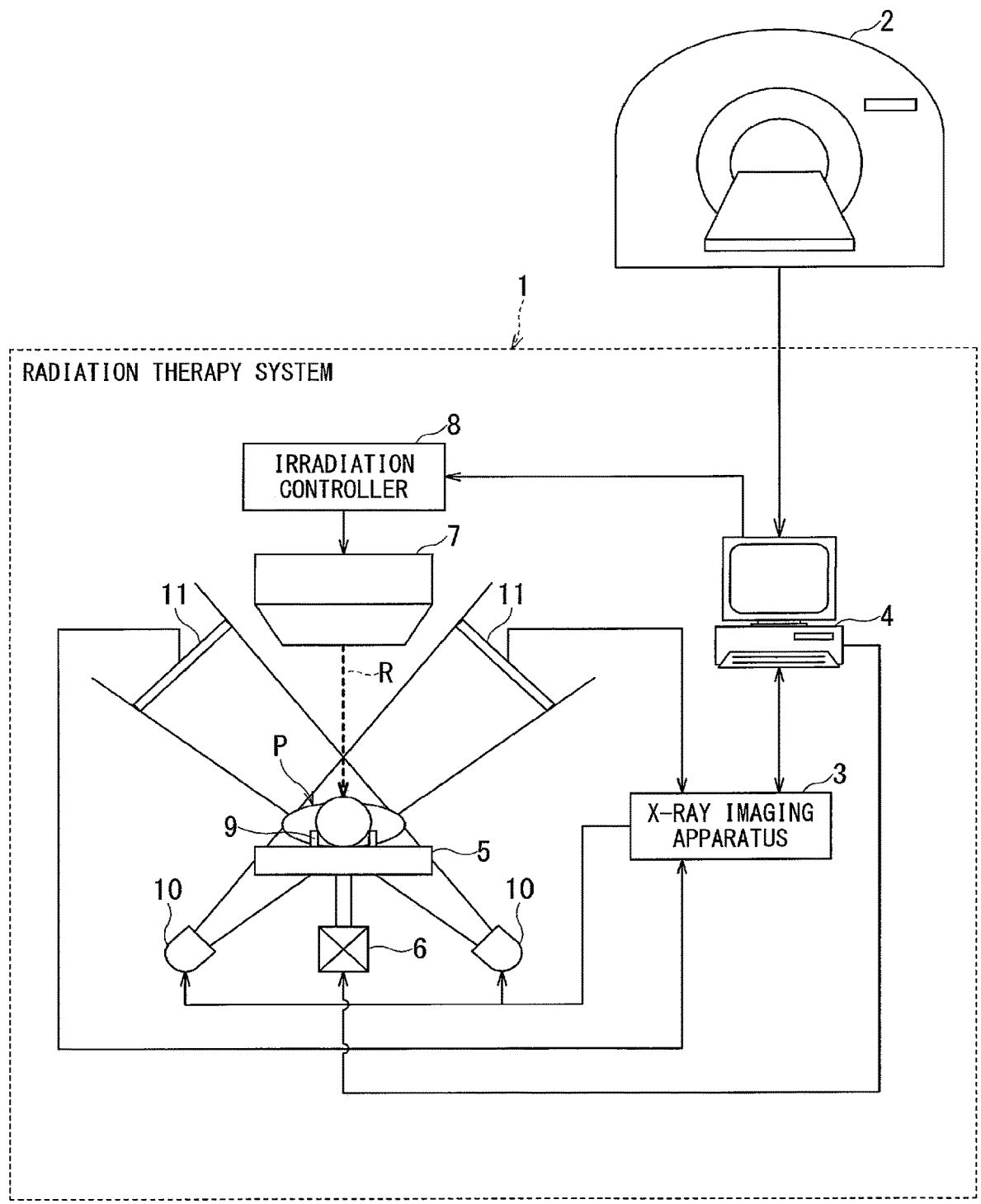
FIG. 1 is a configuration diagram illustrating the radiation therapy system according to the first embodiment.

As shown in FIG. 1, a three-dimensional volume image is acquired when a treatment plan using the radiation therapy system 1 is prepared. For instance, first, computed tomography of the patient (i.e., object) P is performed. In the present embodiment, a medical examination apparatus 2 is provided for performing various examinations of the patient P by computed tomography. This medical examination apparatus 2 is, e.g., configured as an X-ray CT apparatus. A three-dimensional volume image (fluoroscopic image) of the patient P is generated by using the medical examination apparatus 2. The three-dimensional volume image is composed of, e.g., voxel data.

Although an X-ray CT apparatus is exemplified as the medical examination apparatus 2 in the present embodiment, the medical examination apparatus (i.e., diagnostic apparatus) 2 may be any other apparatus that can acquire a three-dimensional volume image of the patient P. For instance, the medical examination apparatus 2 may be an MRI (Magnetic Resonance Imaging) apparatus or an ultrasonic diagnostic apparatus.

Figure 3:
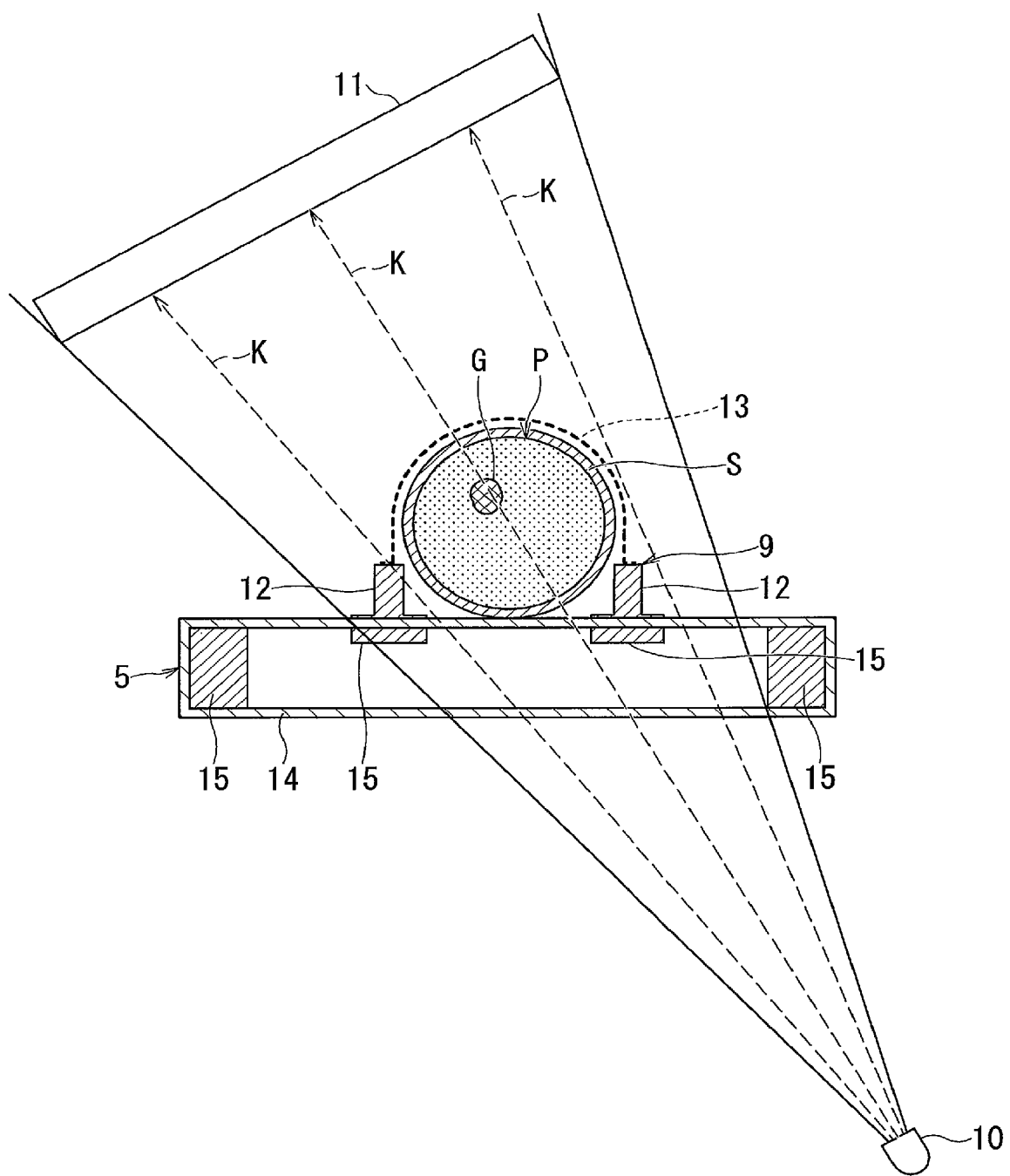
FIG. 3 is a schematic diagram illustrating relationship between an X-ray irradiator, an X-ray detector, and an object.

The radiation therapy system 1 of the present embodiment includes an X-ray imaging apparatus (i.e., fluoroscopic imaging apparatus) 3, a positioning apparatus 4, a mounting table 5, a table driving device 6, a radiation irradiation apparatus 7, and an irradiation controller 8. The X-ray imaging apparatus 3 performs fluoroscopic imaging on the patient P so as to generate X-ray images 40 (i.e., fluoroscopic images included in the category of radiographic images, see FIG. 6) of the patient P. The positioning apparatus 4 performs positioning of the patient P on the basis of the X-ray image 40. The patient P is placed on the mounting table 5. The table driving device 6 changes the position of the mounting table 5. The radiation irradiation apparatus 7 irradiates the legion area G of the patient P with radioactive rays R. The irradiation controller 8 controls the radiation irradiation apparatus 7. In addition, the patient P is fixed by a fixture 9 in the state of being placed on the mounting table 5 (FIG. 3).

The positioning apparatus 4 of the present embodiment includes hardware resources such as a CPU (Central Processing Unit), a ROM (Read Only Memory), a RAM (Random Access Memory), and a HDD (Hard Disc Drive), and is configured as a computer in which information processing by software is achieved with the use of the hardware resources by causing the CPU to execute various programs.

Further, the object positioning method of the present embodiment is achieved by causing the computer to execute the various programs.

In addition, the positioning apparatus 4 is connected to the medical examination apparatus 2, the X-ray imaging apparatus 3, the table driving device 6, and the irradiation controller 8. Further, the X-ray imaging apparatus 3 includes plural X-ray irradiators 10 configured to irradiate the patient P with X-rays and plural X-ray detectors 11 configured to detect X-rays transmitted through the patient P. Moreover, each of the X-ray detectors 11 is configured of, e.g., a flat panel detector (FPD) or an image intensifier.

In the present embodiment, a total of two pairs of the X-ray irradiator 10 and the X-ray detector 11 are provided in such a manner that X-ray imaging is performed simultaneously from two different directions by using the two pairs of the X-ray irradiators 10 and the X-ray detectors 11. It should be noted that a moving image composed of time-sequential X-ray images 40 may be generated by time-sequentially and consecutively performing X-ray imaging on the patient P.

In actual X-ray imaging, two pairs of the X-ray irradiator 10 and the X-ray detector 11 are used for generating a pair of X-ray images 40 that are imaged from respective two directions (e.g., from the right side and the left side of the patient P). Further, a pair of images are also obtained for the DRR (Digitally Reconstructed Radiograph) images 50 to be described below. By using the pair of the X-ray images 40 and the pair of the DRR images 50, three-dimensional positioning can be performed. However, in order to assist understanding by simplifying the configuration, the following description is given by exemplifying each X-ray image 40 and each DRR image 50 that are obtained by imaging the patient P from one direction (FIG. 6A to FIG. 15B).

As shown in FIG. 3, when radiotherapy is performed, the patient P is placed or typically laid down on the mounting table (i.e., bed) 5. For instance, in the case of treatment for, e.g., a brain tumor, the head of the patient P where the lesion area G exists is fixed with the fixture 9. The fixture 9 includes a metallic fixing member 12 fixed to the mounting table 5 and a resin-made medical restraint 13 configured to cover the face of the patient P. In addition, the mounting table 5 includes, e.g., a resin-made table body 14 and a metallic frame 15 provided inside the table body 14. Although a description will be given of the case where the lesion area G exists in the head as one case, the application target of embodiments of the present invention is not limited to such a case. The embodiments of the present invention can also be applied to a case where the lesion area (typically, a tumor) G exists at any part of the whole body.

Since the metallic components such as the fixing member 12 and the frame 15 are hard to transmit X-rays, those metallic components are clearly depicted in each X-ray image 40. In addition, since the resin-made components such as the medical restraint 13 and the table body 14 are easy to transmit X-rays, the resin-made components hardly appear in each X-ray image 40. Further, in the X-ray imaging apparatus 3, the output of X-rays is adjusted in such a manner that the portion of the bone S is most clearly depicted in each X-ray image among the parts constituting the human body. Under this output adjustment, X-rays radiated from the X-ray irradiators 10 are detected by the X-ray detectors 11, and each X-ray image 40 depicting the portion of the bone S is acquired.

In addition, the portion of the bone S of the patient P depicted in each X-ray image 40 serves as an index region that is an index (i.e., indicator) of positioning in the present embodiment. Further, all the other portions except the bone S are defined as non-index regions, such as the respective regions of the mounting table 5 and the fixture 9. It should be noted that each internal organ constituting the human body is a portion other than the bone S and thus is treated as the non-index region in each X-ray image 40.

Further, at the time of treatment planning, one or plural DRR image 50 in which only the portion of the bone S of the patient P is depicted is generated on the basis of the three-dimensional volume image. Moreover, a reference image is defined as the DRR image 50 generated such that the bone S exists at a position suitable for radiation irradiation. Subsequently, the positioning of the patient P is performed by moving the mounting table 5 in such a manner that the position of the bone S appearing in the DRR image (i.e., reference image) 50 matches the position of the bone S appearing in the X-ray image 40 imaged at the time of radiotherapy (FIG. 7). In the present embodiment, the position of the radiation irradiation apparatus 7 is fixed.

It should be noted that there is a time difference of several weeks from completion of treatment plan to actual start of treatment in general. For this reason, the positional relationship between the patient P and each system component such as the mounting table 5 and the fixture 9 differ between at the time of treatment planning and at the time of radiotherapy in some cases. In addition, the respective positions of the patient P and the radiation irradiation 7 assumed at the time of treatment planning differ from the respective positions of the patient P and the radiation irradiation 7 at the time of radiotherapy in some cases. For this reason, it is necessary to accurately perform the matching processing between the DRR image 50 based on the three-dimensional volume image acquired at the time of treatment planning and the X-ray image 40 imaged at the time of radiotherapy.

Figure 6A:
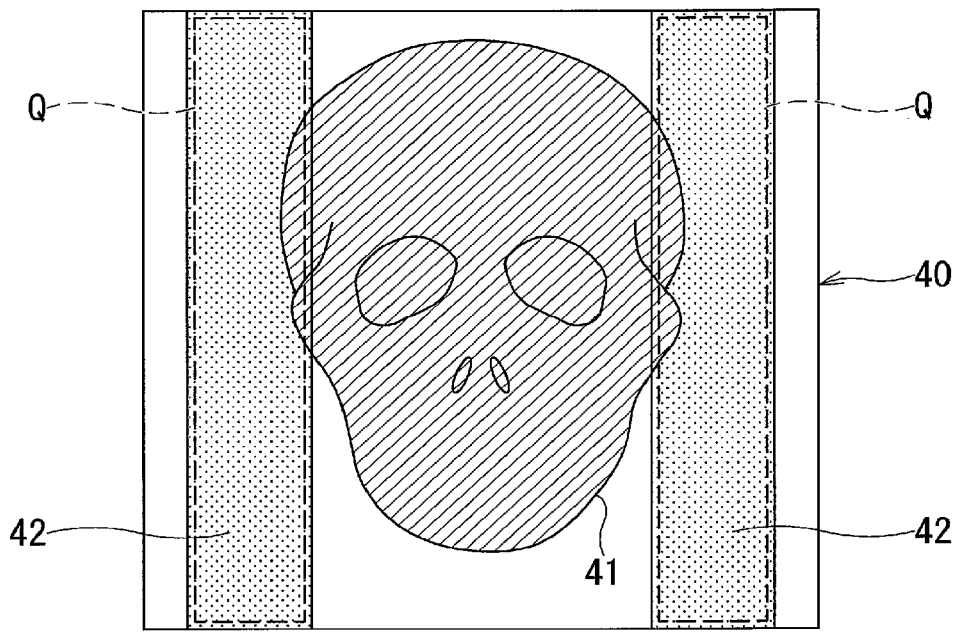
FIG. 6A is a schematic diagram illustrating image processing on an X-ray image before removing a specific region.
Figure 6B:
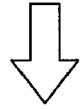
FIG. 6B is a schematic diagram illustrating image processing on an X-ray image after removing the specific region.

However, pixel regions of the metal components in the fixture 9 and the mounting table 5 are included in each X-ray image 40. When the matching processing between the X-ray image 40 and the DRR image is performed in the state where such pixel regions of the metal components are included in the X-ray image 40, the pixel regions depicting the fixture 9 and the mounting table 5 become an obstacle to the matching processing and reduces positioning accuracy. For this reason, preliminary image processing is performed in such a manner that unnecessary pixel regions except the pixel region of the bone S in the X-ray image 40 is removed from the X-ray image 40 prior to the matching processing in the present embodiment (FIG. 3, FIG. 6A and FIG. 6B).

Figure 6B:
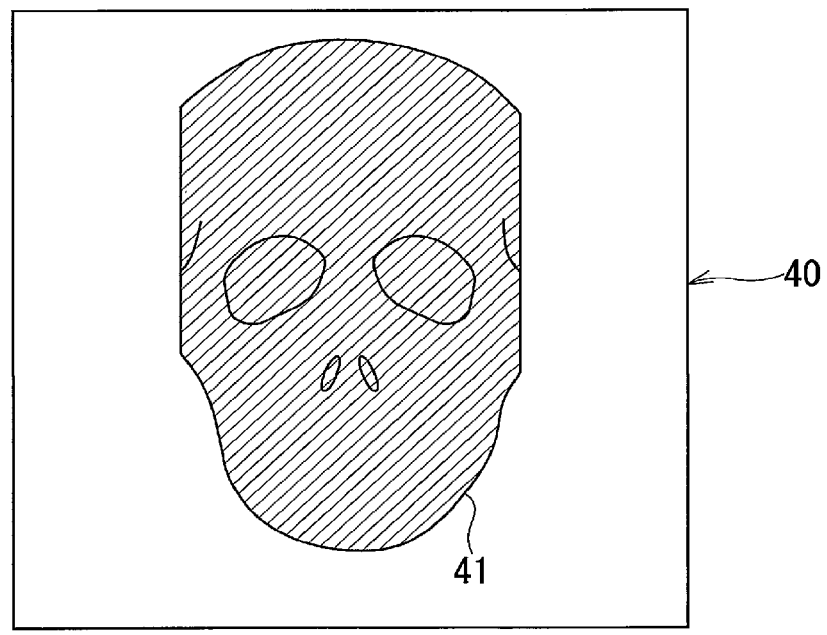

In the following description, out of the pixel regions included in each X-ray image 40, each pixel region depicting the bone S (i.e., index region) of the patient P is referred to as the first region 41 in some cases. Contrastively, out of the pixel regions included in each X-ray image 40, each pixel region outside the patient P (i.e., non-index region that depicts an object except the patient, such as the fixture 9) is referred to as the second region 42 in some cases (FIG. 6). Further, the pixel region of the bone S depicted in each DRR image 50 is referred to as the reference region 51 in some cases (FIG. 7).

As shown in FIG. 1, the positioning apparatus 4 is connected to the irradiation controller 8. In addition, the irradiation controller 8 is connected to the radiation irradiation apparatus 7. Further, the irradiation controller 8 controls the radiation irradiation apparatus 7 in such a manner that the radiation irradiation apparatus 7 starts radiation of the radioactive rays R when the irradiation controller 8 receives an irradiation start signal outputted from the positioning apparatus 4.

Figure 2:
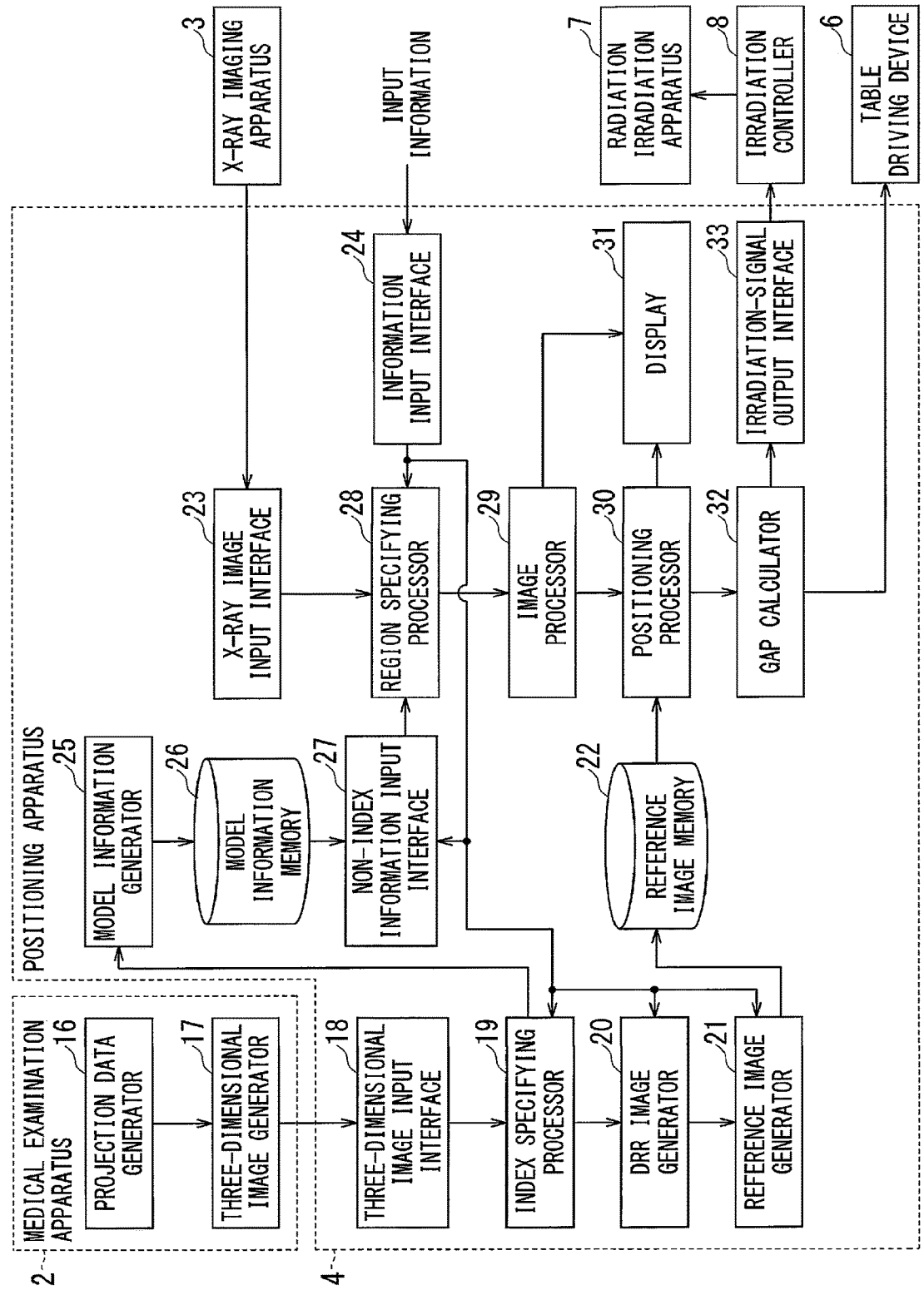
FIG. 2 is a block diagram illustrating the positioning apparatus according to the first embodiment.

As shown in FIG. 2, the medical examination apparatus 2 includes a projection data generator 16 configured to generate projection data (i.e., fluoroscopic image data) obtained by imaging the patient P from plural directions, and also includes a three-dimensional image generator 17 configured to generate a three-dimensional volume image in three dimensions of the patient P on the basis of the plural tow-dimensional projection data to be acquired from the projection data generator 16. Note that each three-dimensional volume image includes information of plural voxels. Further, the three-dimensional image generator 17 outputs each three-dimensional volume image to the positioning apparatus 4.

In addition, the medical examination apparatus 2 may generate a stereoscopic moving image of the patient P by time-sequentially and continuously performing computed tomography. For instance, when the lesion area G is an area that moves inside the patient P, it is possible to acquire information on the three-dimensional movement of the lesion area G.

Further, as shown in FIG. 2, the positioning apparatus 4 includes a three-dimensional image input interface (i.e., three-dimensional image acquisition interface or three-dimensional image acquisition unit) 18, an index specifying processor (i.e., index identifying unit) 19, a DRR image generator (i.e., DRR image generation unit or reconstructed image generator) 20, a reference image generator (i.e., reference image generation unit) 21, and a reference image memory (i.e., reference image storage unit) 22. The three-dimensional image input interface 18 acquires the three-dimensional volume image of the patient P from the medical examination apparatus 2. The index specifying processor 19 specifies each index region and each non-index region, both of which are included in the three-dimensional volume image. The DRR image generator 20 generates the DRR image 50 of the index region on the basis of the three-dimensional volume image. The reference image generator 21 generates the DRR image 50, which is treated as the reference image, on the basis of the image generated by the DRR image generator 20. The reference image memory 22 stores the generated reference image (i.e., DRR image 50).

Here, the DRR image generator 20 generates the DRR image (Digitally Reconstructed Radiograph) 50 on the basis of the three-dimensional volume image and geometry information of the X-ray imaging apparatus 3. The DRR image 50 is an image virtually generated on the basis of the three-dimensional volume image in such a manner that the DRR image 50 has the same composition as the X-ray image 40 imaged by using the X-ray imaging apparatus 3. In addition, the X-ray image 40 and the DRR image 50 are images having substantially the same composition. The above-described index specifying processor 19 performs processing of specifying the index region(s) and the non-index region(s), but does not perform processing of deleting the pixel region of the non-index region (s). Further, in the DRR image 50 generated by the DRR image generator 20, regions objects except the patient P (hereinafter, sometimes referred to as extraneous regions) are depicted, such as the fixture 9.

In addition, the reference image generator 21 generates the DRR image 50 to be treated as the reference image by removing extraneous regions (i.e., the non-index regions such as the fixture 9, and a part of the index region superimposed on this non-index region) from the DRR image 50 that is generated by the DRR image generator 20. The generated reference image (i.e., DRR image 50) is stored in the reference image memory 22. In this manner, since only the pixel region corresponding to the portion left without being removed in the first region 41 (i.e., the index region) is included in the DRR image 50 to be treated as the reference image, it is possible to improve the matching accuracy between the X-ray image 40 and the DRR image 50.

Note that the geometry information includes parameters indicative of the respective positions of the X-ray irradiators 10, the respective positions of the X-ray detectors 11, and the direction of the plane on which the X-ray detectors 11 detect X-rays. This geometry information is configured on the basis of data such as design data (e.g., CAD data) of the X-ray imaging apparatus 3 in advance. This geometry information is input information to be inputted to the information input interface 24 as described below.

In addition, the geometry information may be inputted by a user (e.g., a doctor) at the time of treatment planning or may be acquired from an external device. Further, the DRR image generator 20 may store the geometry information in advance. When the X-ray imaging apparatus 3 is movable, the information input interface 24 may consecutively acquire the geometry information of each state of the X-ray imaging apparatus 3 that changes according to the movement of the movable components of the X-ray imaging apparatus 3 or may store the geometry information of each state in advance.

Moreover, the three-dimensional volume image imaged by the medical examination apparatus 2 includes respective pixel regions of the mounting table 5 and the fixture 9 in addition to the pixel regions of the patient P. Furthermore, the pixel regions of the patient P includes pixels region depicting the bone S and other pixel regions depicting tissues except the bone S. The CT values of these pixel regions are different from each other. The index specifying processor 19 of the positioning apparatus 4 can specify the pixel region of the bone S of the patient P and the other pixel regions (i.e., non-index regions) by analyzing the CT values of the three-dimensional volume image. In addition, the input information inputted to the information input interface 24 may be used for specifying the non-index regions (i.e., pixel regions excluding the bone S).

It should be noted that the work of specifying the respective pixel regions of the bone S and the other parts may be performed on the basis of the input operation to be performed by the user at the time of treatment planning. For instance, the user may perform an input operation to specify the pixel region of the bone S included in the three-dimensional volume image. Further, in order to assist the user, the computer (i.e., the positioning apparatus 4) may be configured to automatically specify the pixel region of the bone S so that the user can modify the specified pixel region.

As shown in FIG. 2, the positioning apparatus 4 further includes an X-ray image input interface (i.e., X-ray image acquisition unit) 23, an information input interface (i.e., information input unit) 24, a model information generator (i.e., model information generation unit) 25, and a model information memory (i.e., model information storage unit) 26. The X-ray image input interface 23 acquires X-ray images 40 that are generated by causing the X-ray imaging apparatus 3 to image the patient P. Various types of information such as the arrangement state of the mounting table 5 are inputted to the information input interface 24. The model information generator 25 generates the three-dimensional model information of each non-index region. The model information memory 26 stores the three-dimensional model information of each non-index region.

In addition, the various types of information inputted to the information input interface 24 include, e.g., geometry information of the X-ray imaging apparatus 3, table information indicative of the arrangement state of the mounting table 5 on which the patient P is placed, and fixture information indicative of the arrangement state of the fixture 9 for fixing the patient P. In the information input interface 24, various types of information may be inputted by the user, or various types of information may be inputted from another device via a network.

Further, the model information generator 25 generates, e.g., the three-dimensional model information of the non-index regions on the basis of the non-index regions (i.e., pixel regions except the bone S specified by the above-described index specifying processor 19). Typically, the model information generator 25 acquires the three-dimensional volume image of the non-index regions by separating the index region (i.e., the pixel region of the bone S) and the non-index regions (i.e., pixel regions except the bone S) in the three-dimensional volume image from each other. Thereafter, on the basis of the three-dimensional volume image of the separated non-index regions, the model information generator 25 generates the three-dimensional model information of the non-index regions.

For instance, the model information generator 25 divides the three-dimensional volume image into plural regions by using pixel values (voxel values) and spatial continuity of pixels so as to determine the index region and the non-index regions on the basis of information of each divided region such as the average pixel value, size, shape, and positional relationship between respective regions.

Additionally or alternatively, previously prepared labels may be assigned to respective pixels so that the three-dimensional volume image is divided into plural regions on the basis of these labels. For instance, an index label is assigned to each pixel in the index region, and an image in which a non-index label is assigned to each pixel in each non-index region is prepared in advance. Further, a dictionary for calculating the likelihood of the non-index region for each pixel is generated according to the feature extracted from the peripheral pattern of the pixels of this image. By applying the dictionary to each pixel of the three-dimensional volume image, the likelihood of the non-index region is calculated and then threshold processing is performed to separate the pixels of each non-index region. When there is information indicative of the non-index region(s) being inputted at the time of treatment planning, the three-dimensional volume image may be divided on the basis of this information.

In addition, the three-dimensional model information of the non-index regions may include information indicative of the configuration of mechanical components such as the mounting table 5 and the fixture 9 and information indicative of portions constituting the patient P except the bone S. In this manner, the three-dimensional model information of the non-index regions such as the mounting table 5 and the fixture 9 can be acquired from the three-dimensional volume image of the patient P that can be acquired at the time of, e.g., treatment planning. Hence, it is possible to omit the work of separately preparing the three-dimensional model information of the non-index regions (such as design data of the mounting table 5 and the fixture 9). Incidentally, the respective pixel regions of the non-index regions separated from the three-dimensional volume image are generated as the three-dimensional model information and are stored in the model information memory 26.

Although a description has been given of the method in which the three-dimensional model information of the non-index regions is generated on the basis of the three-dimensional volume image as one aspect, the method of generating the three-dimensional model information is not limited the above-described method. For instance, the three-dimensional model information of the non-index regions may be generated by referring to the table information or fixture information inputted to the information input interface 24. Additionally, the three-dimensional model information of the non-index regions may be inputted from a device other than the medical examination apparatus 2, may be inputted from a server for storing medical images, may be inputted from a storage medium such as a CD and a DVD, or may be inputted from another device via a network.

As shown in FIG. 2, the positioning apparatus 4 further includes a non-index information input interface (i.e., non-index information acquisition unit) 27, a region specifying processor (i.e., region identifying unit) 28, an image processor (i.e., image processing unit) 29, a positioning processor (i.e., positioning unit or positioning controller) 30, a display (i.e., monitor) 31, a gap calculator (i.e., difference calculation unit or deviation calculation unit) 32, the table driving device 6, and an irradiation-signal output interface (i.e., irradiation-signal output unit) 33. The non-index information input interface 27 acquires the three-dimensional model information of the non-index regions stored in the model information memory 26. The region specifying processor 28 specifies the second region 42 of each non-index region in the X-ray image 40 on the basis of the three-dimensional model information of each non-index region. The image processor 29 performs image processing on the specified region. The positioning processor 30 performs the positioning of the patient P by performing the matching processing between the first region 41 of the index region of the X-ray image 40 subjected to the image processing and the reference region 51 of the DRR image 50 as the reference image. The display 31 displays the X-ray image 40 subjected to the image processing. The gap calculator 32 calculates gap amount (i.e., deviation amount or difference amount) between the first region 41 of the X-ray image 40 and the reference region 51 of the DRR image 50 as the reference image. The table driving device 6 moves the mounting table 5 on the basis of the gap amount. The irradiation-signal output interface 33 outputs an irradiation start signal when the gap amount is equal to or smaller than a predetermined threshold value.

FIG. 6A illustrates the X-ray image 40 generated by causing the X-ray imaging apparatus 3 to image the patient P. In this X-ray image 40, the first region 41 of the skull S of the patient P and the second regions 42 such as the fixture 9 are depicted. Here, the region specifying processor 28 specifies specific regions Q (shown by the broken-line regions in FIG. 6A), in each of which the second region 42 such as the fixture 9 is depicted in the X-ray image 40, on the basis of the three-dimensional model information of the non-index regions acquired by the non-index information input interface 27 and various types of information inputted to the information input interface 24. In the case of FIG. 6A, a part of each second region 42 is superimposed on a part of the first region 41 (i.e., temporal region of the skull S). Although each of the specific regions Q is a part superimposed on the second region 42, the broken-line regions indicative of the respective specific regions Q are intentionally slightly shifted from the solid-line regions indicative of the respective second regions 42 in FIG. 6A in order to clearly distinguish between both.

In the present embodiment, since the region specifying processor 28 specifies each specific regions Q on the basis of the various types of information inputted to the information input interface 24, it is possible to specify each specific region Q (i.e., the region where the second region 42 appears) in which the way of appearance changes according to the arrangement state of the X-ray imaging apparatus 3, the mounting table 5, and the fixture 9. Incidentally, it is not necessarily required to use all the input information inputted to the information input interface 24, and each specific region Q may be specified by using only one of information items indicative of the arrangement state of each device. In addition, the various types of information inputted to the information input interface 24 may include information on clothes or wearing objects of the patient P.

As shown in FIG. 6B, the image processor 29 performs image processing of eliminating the pixel regions depicted in each specific region Q in the X-ray image 40. In the first embodiment, both the first region 41 and the second regions 42 appearing in the specific region Q are eliminated. In this image processing, it is desirable to replace the pixel value (luminance value) of the specific region Q with a fixed value. For instance, since the pixel value of each pixel of the X-ray image 40 always has a positive value, by replacing each pixel value of the specific region Q with −1, the specific regions Q can be distinguished from the non-specific regions (i.e., pixel regions except the specific regions Q). In this manner, only the first region (s) 41 (part of the skull S) appearing in the specific region remains in the X-ray image 40. That is, the second regions 42 that appear in the specific region Q can be excluded from the matching target of positioning.

Further, the display 31 displays the X-ray image 40 on which the image processing has been performed. A user can see the X-ray image 40 displayed on the display 31. That is, the state of the matching processing performed by the positioning processor 30 can be seen by a user with the use of the display 31. Here, the display 31 displays the X-ray image 40 and the DRR image 50 in such a manner that the X-ray image 40 and the DRR image 50 are superimposed on each other. In addition, the display 31 may display the X-ray image 40 and the DRR image 50 side by side or may alternately display both of the X-ray image 40 and the DRR image 50. In this manner, when positioning of the patient P is performed by using the index region, a user can grasp the matching state by the X-ray image 40 displayed on the display 31. Here, the positioning apparatus 4 may be configured to receive an operation of a user who changes or modifies the X-ray image 40 subjected to image processing.

In the case of displaying the X-ray image 40 subjected to the image processing on the display 31 in the first embodiment, the removed specific region Q may be displayed by a predetermined chromatic color or the pixels of the removed specific region Q may be inverted in black and white to be displayed. Additionally or alternatively, in this case, the specified region Q may be painted in one color and displayed.

Figure 7A:
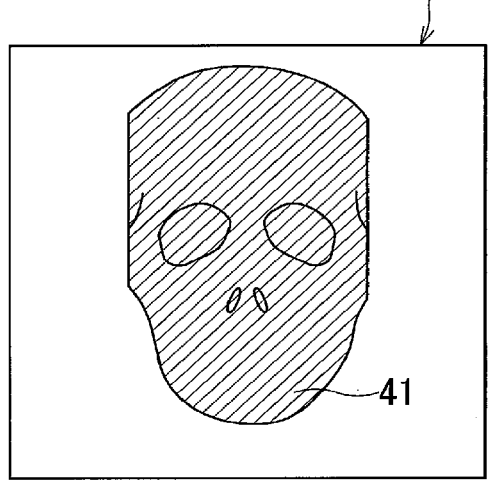
FIG. 7A to FIG. 7C are schematic diagrams illustrating matching processing between an X-ray image and a DRR image.
Figure 7B:
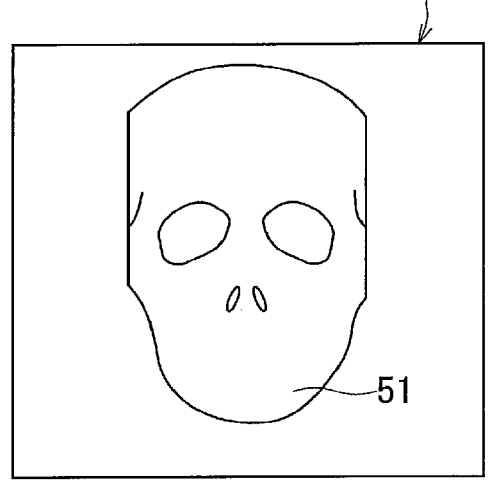
Figure 7C:
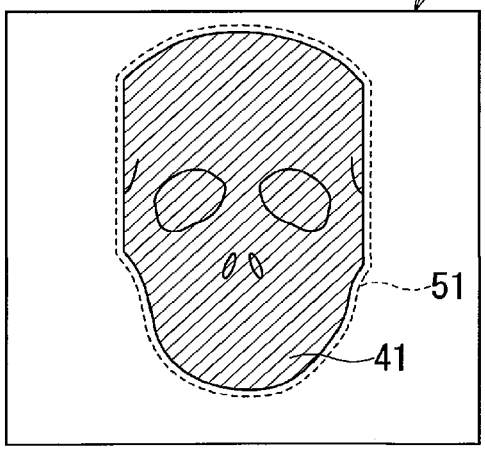

As shown in FIG. 7A to 7C, the positioning processor 30 performs the matching processing between the X-ray image 40 (FIG. 7A) subjected to the image processing and the DRR image 50 (FIG. 7B) so as to start positioning of the patient P. The partial image (i.e., pixel region) in the specific region Q of the DRR image 50 is deleted in advance when the reference image is generated in the reference image generator 21. Further, as a part of the entire positioning operation, the matching processing between the X-ray image 40 and the DRR image 50 is executed until it is determined that a similarity index value (i.e., gap amount of the position of the patient P) between both images becomes equal to or smaller than the threshold value (FIG. 7C). In the present embodiment, the above-described similarity index value between two images indicates the gap amount between the positions of the patient P in the respective images, and it is assumed that a smaller similarity index value indicates higher similarity between both images. Although the reference region 51 is a pixel region superimposed on the first region 41, the broken line indicative of the reference region 51 is intentionally slightly shifted from the solid line indicative of the first region 41 in FIG. 7C in order to easily distinguish between both.

In addition, the gap calculator 32 calculates the similarity index value, which is a value indicative of the gap amount of the position of the patient P, between the X-ray image 40 and the DRR image 50. For instance, when the similarity index value between the X-ray image 40 and the DRR image 50 exceeds the threshold value, the table driving device 6 is driven to move the mounting table 5 on which the patient P is placed. Thereafter, X-ray imaging is performed again to obtain further X-ray images 40. Further, the matching processing between the newly generated X-ray image 40 and the DRR image 50 is performed again. In this manner, the operation from the movement of the mounting table 5 to the matching processing between the updated X-ray image 40 and the DRR image 50 is repeated until the similarity index value between the updated X-ray image 40 and the DRR image 50 becomes equal to or less than the threshold value.

Here, when the coordinate position of each pixel of the DRR image 50 and the X-ray image 40 is defined as (u, v), the pixel value at the pixel position (u, v) of the DRR image 50 is denoted as I(u, v) and the pixel value at the pixel position (u, v) of the X-ray image 40 is denoted as X(u, v). Further, when an error indicative of the similarity index value (i.e., gap amount of the position of the patient P) between the DRR image 50 (i.e., reference image) and the X-ray image 40 (radiographic image) is defined as "e", the error e is calculated by using the following equations (1) and (2). The equations (1) and 2 are equations for calculating the gap amount when the pixel value of each pixel of the specific regions Q of the X-ray image 40 is replaced by −1. Note that $\phi$ in the equations (1) and (2) is a predetermined function.

$$\phi(u, v) = \begin{cases} 0 & \text{if } X(u, v) = -1 \\ (I(u, v) - X(u, v))^2 & \text{otherwise} \end{cases} \quad \text{Equation (1)}$$

$$e = \sum_u \sum_v \phi(u, v) \quad \text{Equation (2)}$$

It is preferable to repeat the operation of X-ray imaging for generating the X-ray image 40 of the patient P and movement of the mounting table 5 until the error e becomes equal to or less than the predetermined threshold value.

After completion of the positioning of the patient P (i.e., when the gap calculator 32 determines that the similarity index value is equal to or smaller than the threshold value), the irradiation-signal output interface 33 outputs the irradiation start signal toward the irradiation controller 8. In addition, when the irradiation controller 8 receives the irradiation start signal outputted from the positioning apparatus 4, the irradiation controller 8 starts irradiation of the radioactive rays R by using the radiation irradiation apparatus 7.

Next, the positioning processing (i.e., positioning method) executed by the positioning apparatus 4 will be described with reference to the flowcharts of FIG. 4 and FIG. 5.

First, at the time of treatment planning, by examining the patient P with the use of the medical examination apparatus 2, the three-dimensional volume image is generated.

Figure 4:
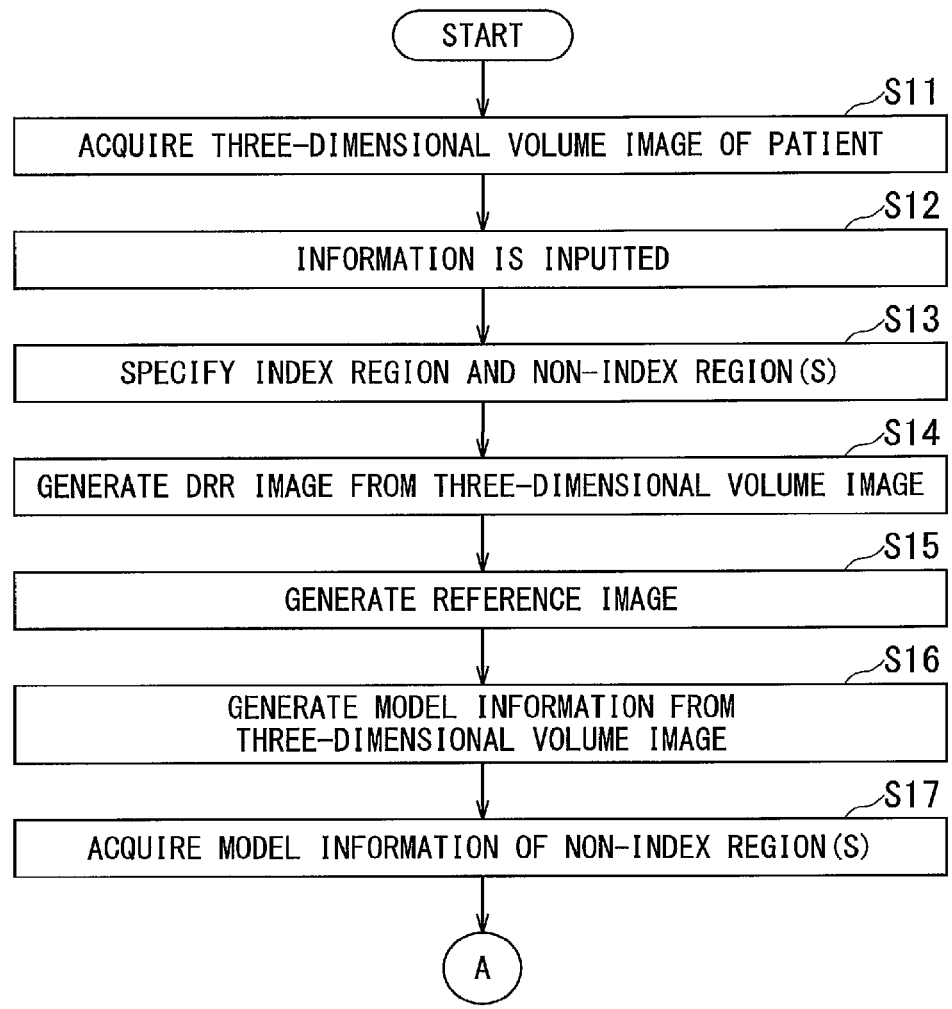
FIG. 4 is a flowchart illustrating the anterior half of positioning processing.

In the step S11 of FIG. 4, the three-dimensional image input interface 18 of the positioning apparatus 4 acquires the three-dimensional volume image from the medical examination apparatus 2.

In the next step S12, information items such as the geometry information of the X-ray imaging apparatus 3, the table information of the mounting table 5, and the fixture information of the fixture 9 are inputted to the information input interface 24.

In the next step S13, the index specifying processor 19 specifies the pixel region of the bone S (i.e., index region) in the three-dimensional volume image and the pixel regions except the bone S (i.e., non-index regions).

In the next step S14, the DRR image generator 20 generates the DRR image 50 on the basis of the three-dimensional volume image and the geometry information of the X-ray imaging apparatus 3.

In the next step S15, the reference image generator 21 removes (i.e., eliminates, deletes, or erases) the pixel regions of the non-index regions such as the fixture 9 from the DRR image 50 generated by the DRR image generator 20 so as to generate the DRR image 50 that is treated as the reference image.

In the next step S16, the model information generator 25 generates the three-dimensional model information of extraneous regions (i.e., the non-index regions such as the fixture 9) on the basis of the three-dimensional volume image in which the pixel region of the bone S (i.e., index region) and the pixel regions except the bone S (i.e., non-index region) are specified.

In the next step S17, the non-index information input interface 27 acquires the three-dimensional model information of the extraneous regions such as the fixture 9.

Figure 5:
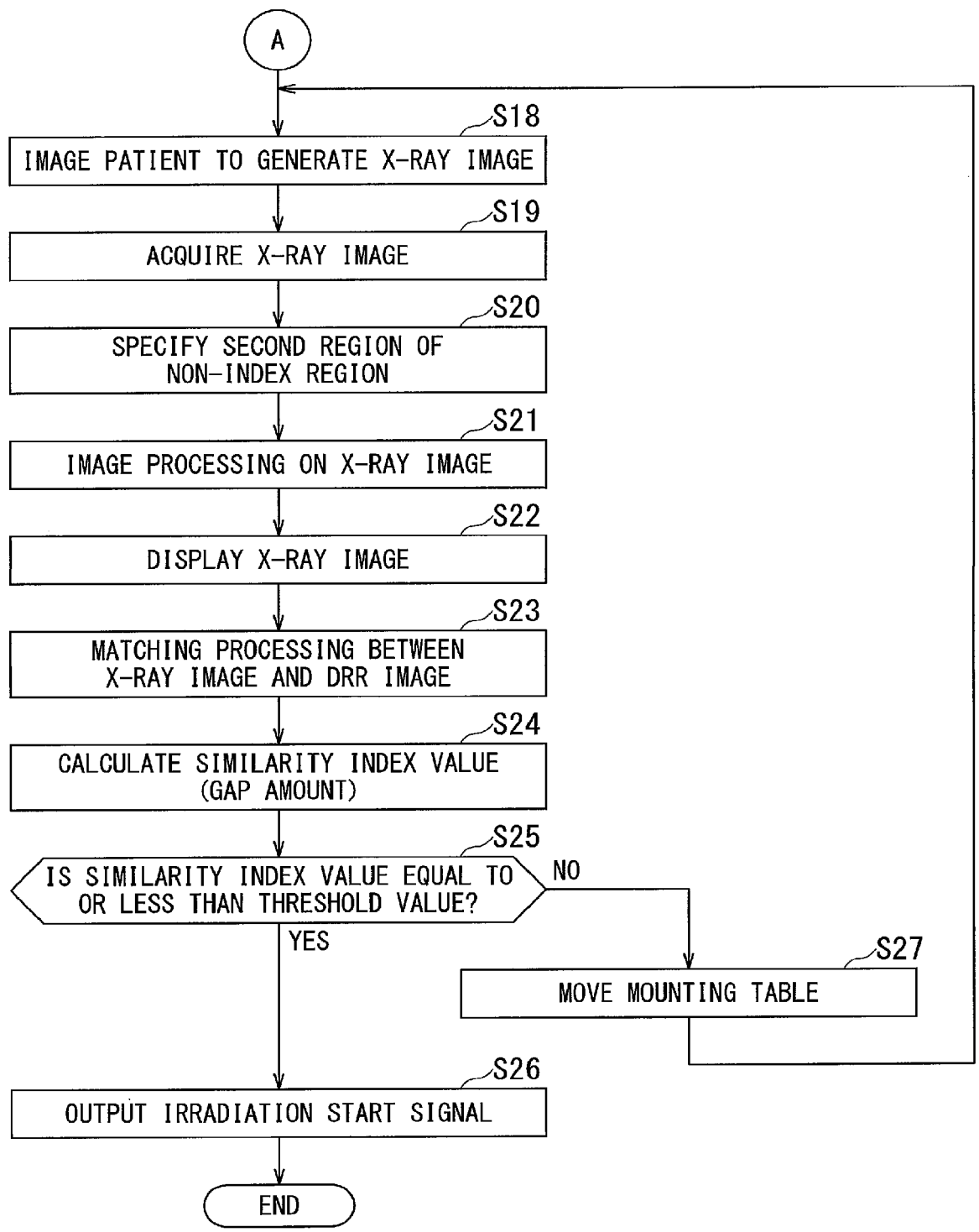
FIG. 5 is a flowchart illustrating the posterior half of the positioning processing subsequent to FIG. 4.

In the next step S18 of FIG. 5, radiotherapy is started. At the start of the radiotherapy, the X-ray imaging apparatus 3 images the patient P so as to generate the X-ray image 40 of the patient P.

In the next step S19, the X-ray image input interface 23 acquires such an X-ray image 40 from the X-ray imaging apparatus 3 that the first region 41 of the bone S (i.e., index region) serving as the index for positioning of the patient P and the second regions 42 (i.e., non-index regions) of other parts except the bone S are included.

In the next step S20, the region specifying processor 28 specifies the specific region Q in which the second regions 42 such as the fixture 9 are depicted in the X-ray image 40.

In the next step S21, the image processor 29 performs image processing of removing the partial image (i.e., pixel region) depicted in the specific region Q of the X-ray image 40.

In the next step S22, the display 31 displays the X-ray image 40 subjected to the image processing.

In the next step S23, the positioning processor 30 performs the matching processing between the X-ray image 40 subjected to the image processing and the DRR image 50 generated as the reference image so as to start the positioning of the patient P.

In the next step S24, the gap calculator 32 calculates the similarity index value between the X-ray image 40 and the DRR image 50, which similarity index value is a value indicative of the gap amount of the position of the patient P between both images.

In the next step S25, the gap calculator 32 determines whether the calculated similarity index value (for evaluating similarity degree between both images) exceeds the threshold value or not.

When the similarity index value is equal to or less than the threshold value, the processing proceeds to the step S26 in which the irradiation controller 8 outputs the irradiation start signal to the irradiation controller 8 and the positioning processing is completed.

Conversely, when the similarity index value exceeds the threshold value, the processing proceeds to the step S27 in which the table driving device 6 is driven to move the mounting table 5 with the patient P placed thereon, and then the processing returns to the step S18. As to the movement of the mounting table 5, the moving direction and/or the moving amount of the mounting table 5 may be adjusted on the basis of on the gap amount (i.e., difference) between the X-ray image 40 and the DRR image 50.

Although a mode in which each step is executed in series is illustrated in the flowcharts of the present embodiment, the execution order of the respective steps is not necessarily fixed and the execution order of part of the steps may be changed. Additionally, some steps may be executed in parallel with another step.

In the first embodiment, since the region specifying processor 28 specifies the specific region Q (i.e., region including the second region 42) in the X-ray image 40 before execution of the image processing such as removal of the second regions 42, it is not necessary to perform image processing on the entirety of the X-ray image 40. In other words, it is possible to minimize the area (i.e., number of pixels) on which image processing is performed. Thus, real-time processing can be efficiently performed. According to the technique of the first embodiment as described above, it is sufficient to perform the processing on the pixels of the specific region Q, and thus the load of image processing can be reduced as compared with the case where the pixels of the entire image are subjected to the image processing. For instance, at the time of positioning of the patient (object) P, the X-ray imaging apparatus 3 images the patient P again to generate the X-ray image 40 each time the position of the patient P is changed, and thus it is required to process a large number of the X-ray images 40. However, in the first embodiment, it is possible to reduce load of such processing at the time of positioning of the patient P.

Additionally, in the first embodiment, images are two-dimensional X-ray images 40 that are generated by imaging the patient P when positioning of the patient P is performed, and the positioning processor 30 performs the positioning of the patient P by using the DRR image 50 as the reference image. In this manner, when the patient P is imaged for generating a radiographic image used for the positioning, it is sufficient to generate a two-dimensional X-ray image 40 and thus exposure of the patient P to X-rays can be reduced.

Although the image processor 29 is configured to completely remove both the first region(s) 41 and the second region(s) 42 included in the specific region Q in the first embodiment, it is not necessarily required to completely remove both the first region (s) 41 and the second region (s) 42. For instance, instead of removing both the first region(s) 41 and the second region(s) 42, the pixel value of each pixel of the first and second regions 41 and 42 included in the specific region Q may be reduced to become lower than the pixel value of each pixel of the first region 41 that is positioned outside the specific region Q.

In the first embodiment, the three-dimensional model information of the non-index region(s) is generated on the basis of the three-dimensional volume image that is generated by imaging the patient P at the time of treatment planning. However, the three-dimensional model information may be acquired by another method. For instance, the three-dimensional model information of the non-index region(s) may be inputted from the outside.

Next, a description will be given of the image processing on the X-ray image 40 according to one modification of the first embodiment, by referring to FIG. 8A to FIG. 9C. Note that the same reference signs are assigned to the same components as the above-described first embodiment in each figure, and duplicate description is omitted.

Figure 8A:
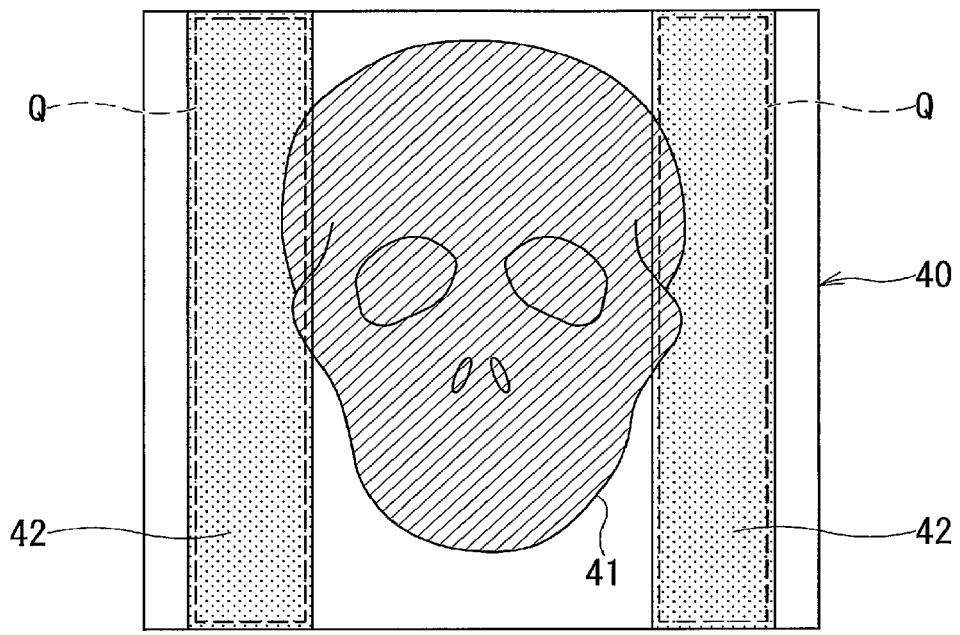
FIG. 8A and FIG. 8B are schematic diagrams illustrating image processing on an X-ray image before and after removing the second pixel region according to one modification of the first embodiment.

As shown in FIG. 8A, the X-ray image 40 (i.e., fluoroscopic image included in the category of radiographic image) includes the first region 41 of the skull S of the patient P and the second regions 42 such as the fixture 9. Here, the region specifying processor 28 specifies the specific region Q in which the second region(s) 42 such as the fixture 9 is included in the X-ray image 40, on the basis of the three-dimensional model information of the non-index region(s) acquired by the non-index information input interface 27 and various types of information inputted to the information input interface 24. In the case of FIG. 8A, a part of each of the second regions 42 is superimposed on a part of the first region 41 (i.e., temporal portion of the skull S). Although each specific region Q is a part superimposed on each second region 42, the broken-line regions indicative of the respective specific regions Q are intentionally slightly shifted from the solid-line regions indicative of the respective second regions 42 in FIG. 8A in order to easily distinguish between them.

Figure 8B:
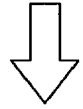
Figure 8B:
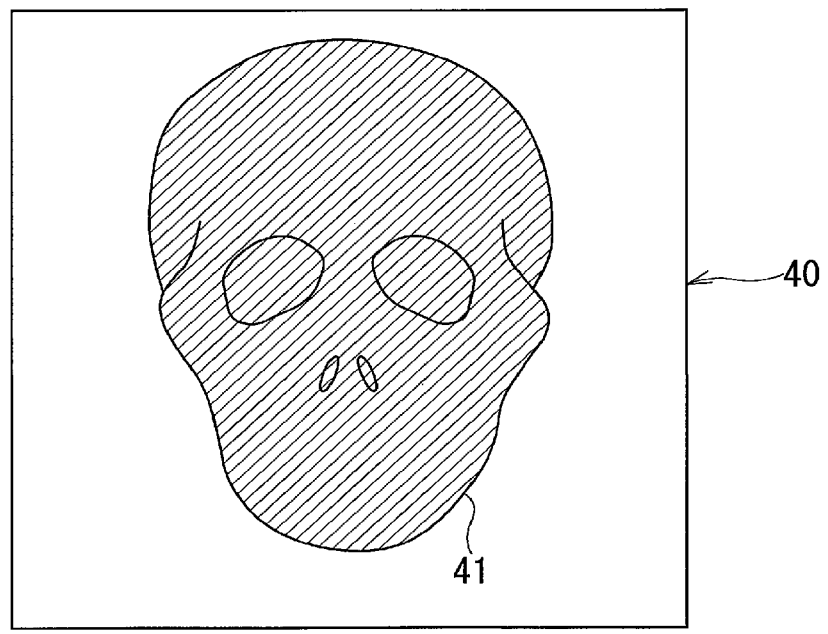

In the image processing of the step S21 as a part of the above-described positioning processing, the image processor 29 removes every second region 42 included in the specific regions Q in the X-ray image 40 as shown in FIG. 8B. Although both the first region(s) 41 and the second region(s) 42 in the specific region Q are removed in the case of the above-described first embodiment, in this modification, the first region 41 included in the specific region Q is left while only the second regions 42 are removed.

In this image processing, on the basis of the DRR image 50 (FIG. 9B) generated by the DRR image generator 20, the pixel values (or luminance value) of the respective pixels of the second region(s) 42 expected to be included in the X-ray image 40 are calculated in advance. The calculated pixel values correspond to the respective pixels of the image. Further, by subtracting the calculated pixel values of the second region(s) 42 from the respective pixel values of the actually generated X-ray image 40, only the second region(s) 42 can be removed. Although the reference region 51 is a region superimposed on the first region 41, the broken line indicative of the reference region 51 Q is intentionally slightly shifted from the solid line indicative of the first region 41 in FIG. 9C in order to easily distinguish between both.

Figure 9A:
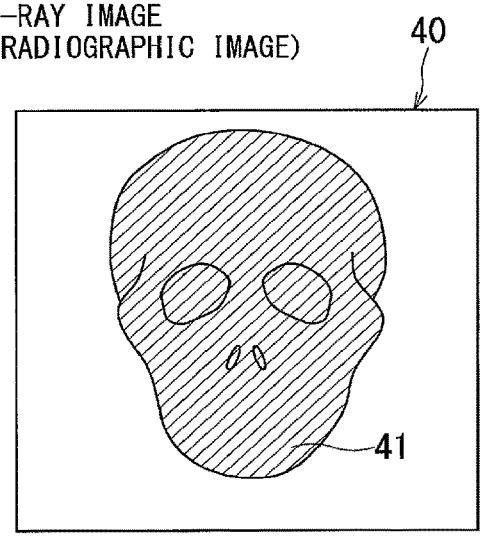
FIG. 9A to FIG. 9C are schematic diagrams illustrating the matching processing between the X-ray image and the DRR image in the modification following FIG. 8B.
Figure 9B:
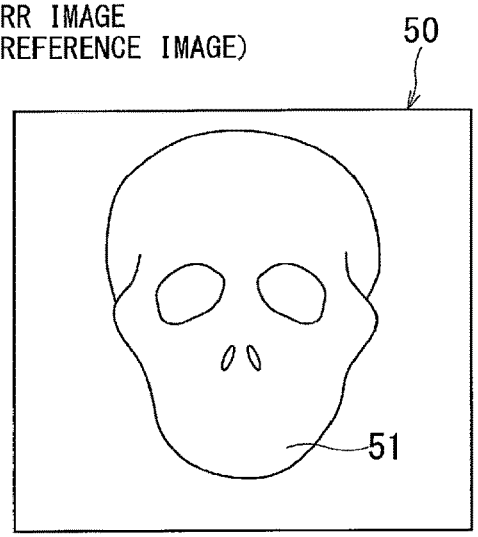
Figure 9C:
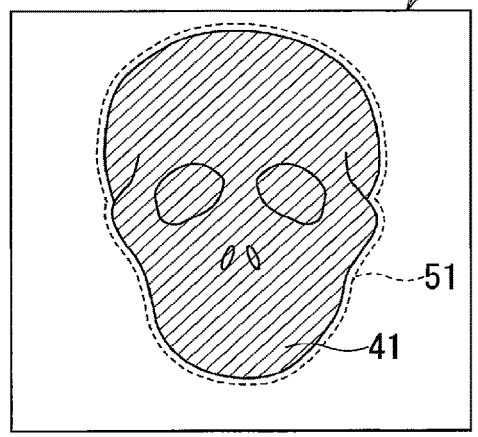

In this manner, even when a part of each second region 42 overlaps the first region 41, only the second regions 42 are removed and the entirety of the first region 41 (region of the skull S) is left (FIG. 9A), which facilitates the positioning with the use of the index region as an index (FIG. 9C). As to the image processing of removing only the second region(s) 42 in the case where the second region(s) 42 partially overlaps the first region 41, various types of imaging processing can be applied.

Although the image processor 29 completely removes the second region(s) 42 in the above-described modification, the second region 42 may not be completely removed. For instance, the pixel values of the respective pixels of the second region 42 may be reduced so as to become lower than the pixel value of each pixel of the first region 41. Although the entirety of each first region 41 remains in the X-ray image 40 after the image processing, instead of such image processing, the pixel values of the respective pixels of the first region 41 included in the specific region Q may be reduced. In this case, it is sufficient that the reduction amount of each pixel value of the first region 41 is smaller than the reduction amount of each pixel value of the second region(s) 42.

In the case of displaying the X-ray image 40 subjected to the image processing on the display 31 in the modification, each region where the second region 42 is removed may be displayed with a predetermined chromatic or achromatic color. In this case, a difference image between the X-ray image 40 before removing the second region(s) 42 and the X-ray image 40 subjected to the processing of removing the second region(s) 42 may be displayed. Also in this case, the display 31 may switch between display of the X-ray image 40 before removing the second region(s) 42 and display of the X-ray image 40 subjected to the processing of removing the second region(s) 42.

Next, a description will be given of an image processing technique of another modification in which only the second region(s) 42 is removed from the X-ray image 40, with reference to FIG. 10A to FIG. 15B. In order to aid understanding, FIG. 10A to FIG. 15B exemplify a case where the fixture 9 (i.e., the second region 42, the non-index region) is depicted in the vicinity of the center of the skull S (i.e., the first region 41, the index region) of the X-ray image 40 (i.e., fluoroscopic image included in the category of radiographic image). The line L in each of FIG. 10A to FIG. 15B is at the same position.

In addition, it is assumed that the portions being hard to transmit X-rays such as the bone S and the fixture 9 are darkly depicted in the X-ray image 40. Further, in each X-ray image 40, a luminance value of a bright region is large and a luminance value of a dark region is small. In other words, a region having a small luminance value contains information constituting the first region 41 indicative of the shape of the bone S or the second region 42 indicative of the shape of the fixture 9 in some cases.

It should be note that the X-ray image 40 can be inverted in brightness (i.e., subjected to monochrome inversion or black-and-white reversal). In the case of performing black-and-white reversal, a portion that is hard to transmit X rays may appear bright on the X-ray image 40 in some cases. The term "bright" and "dark" and the magnitude of the luminance value in the following description can be arbitrarily changed according to the black-and-white reversal of the X-ray image 40.

Figure 10A:
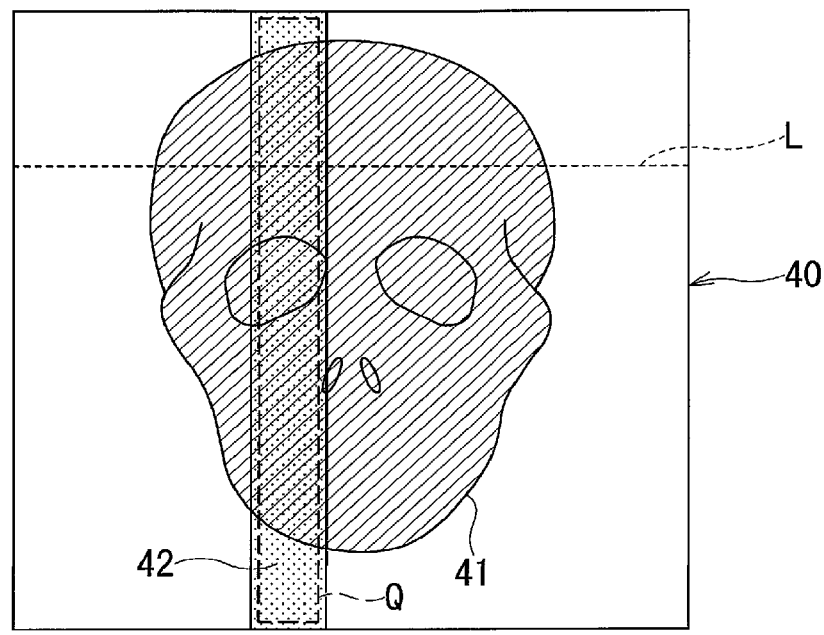
FIG. 10A and FIG. 10B are schematic diagrams illustrating the image processing technique according to another modification of the first embodiment.

FIG. 10A illustrate an X-ray image 40 before image processing. In this X-ray image 40, the first region 41 of the skull S of the patient P and the second region 42 of the fixture 9 are included. Although the specific region Q is a region superimposed on the second region 42, the broken-line region indicative of the specific region Q is intentionally slightly shifted from the solid-line region indicative of the second region 42 in FIG. 10A in order to clearly distinguish between both. In addition, in the graph of FIG. 10B, the horizontal axis indicates the position on the line L of the X-ray image 40 (i.e., u-axis), and the vertical axis indicates the luminance value (i.e., brightness) of each pixel corresponding to the line L of the X-ray image 40. In the X-ray image 40, the luminance value 43 of the first region 41 is small, and the smallest luminance value is the luminance value 44 of the portion where the first region 41 is superimposed on the second region 42.

Figure 11A:
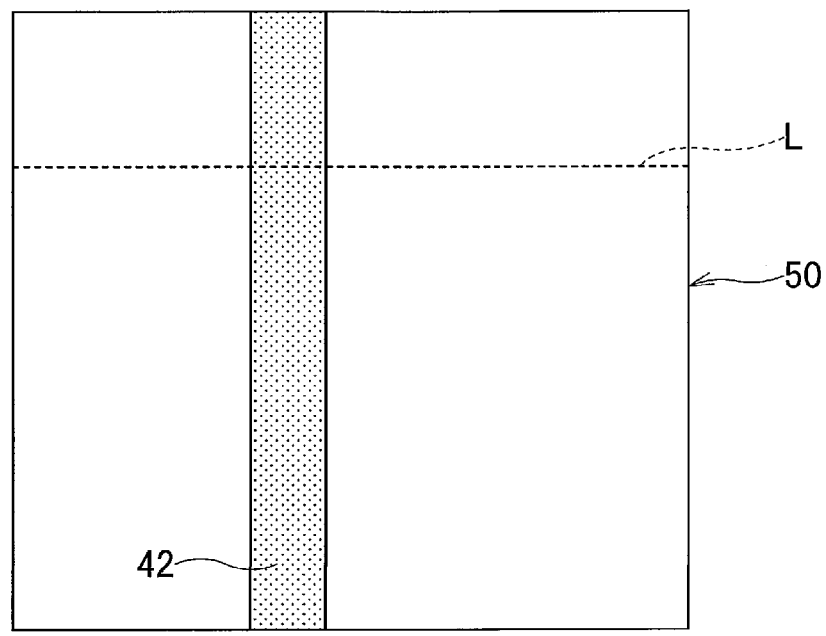
FIG. 11A and FIG. 11B are schematic diagrams illustrating the image processing technique according to the modification following FIG. 10B.
Figure 11B:
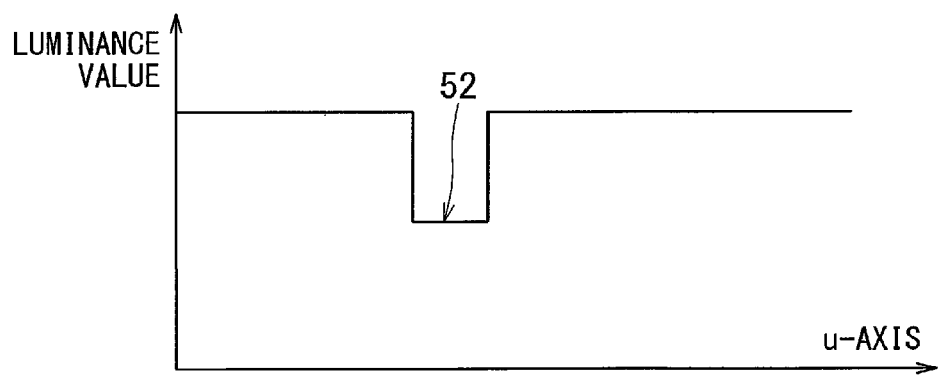

FIG. 11A illustrates the DRR image 50 in which the second region 42 of the fixture 9 is included. This DRR image 50 is generated on the basis of the three-dimensional model information of the non-index region(s). In the graph of FIG. 11B, the horizontal axis indicates the position on the line L of the DRR image 50 (i.e., u-axis), and the vertical axis indicates the luminance value (i.e., brightness) of each pixel corresponding to the line L of the DRR image 50. In the DRR image 50, the luminance value 52 of the second region 42 is small.

Figure 10B:
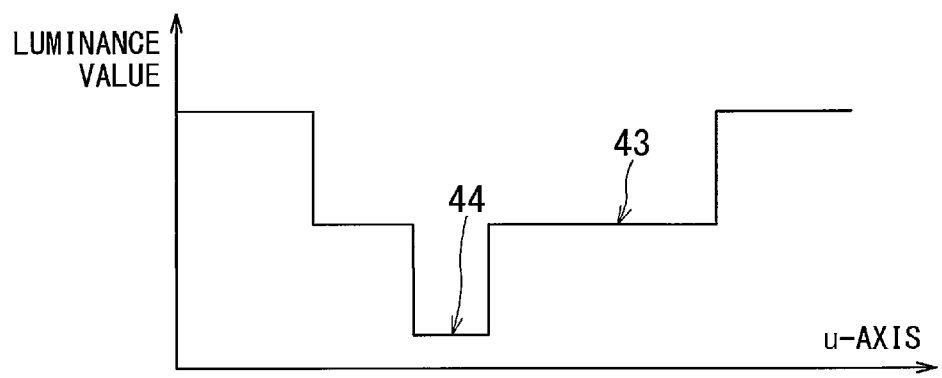
Figure 12A:
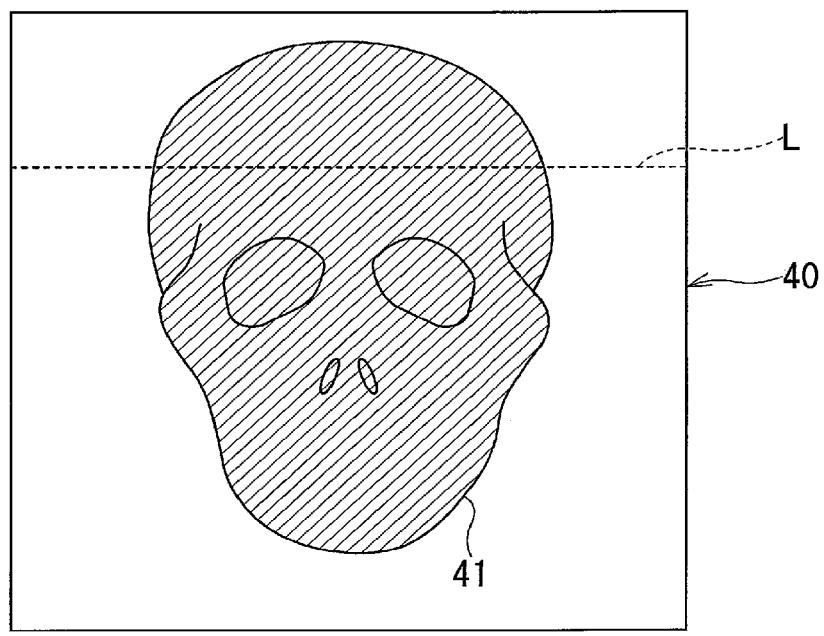
FIG. 12A and FIG. 12B are schematic diagrams illustrating the image processing technique according to the modification following FIG. 11B.
Figure 12B:
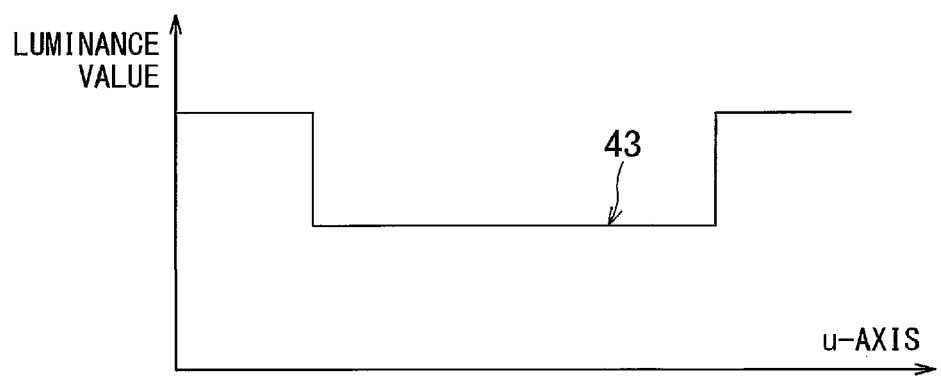

FIG. 12A illustrates the X-ray image 40 subjected to the image processing. In this X-ray image 40, the second region 42 of the fixture 9 is removed and only the skull S of the patient P is depicted as the first region 41. In the graph of FIG. 12B, the horizontal axis indicates the position on the line L of the X-ray image 40 (i.e., u-axis), and the vertical axis indicates the luminance value (i.e., brightness) of each pixel corresponding to the line L of the X-ray image 40. In the X-ray image 40 subjected to the image processing, the smallest luminance value 44 in the above-described FIG. 10B is removed and the luminance value 43 of the first region 41 remains.

The image processing technique for removing only the second region(s) 42 from the X-ray image 40 will be described in detail. When a coordinate position of each pixel of the DRR image 50 and the X-ray image 40 is denoted as (u, v), the pixel value at the pixel position (u, v) of the X-ray image 40 before the image processing shown in FIG. 10A and FIG. 10B is denoted as X(u, v), the pixel value at the pixel position (u, v) of the DRR image 50 shown in FIG. 11A and FIG. 11B is denoted as I(u, v), and the pixel value at the pixel position (u, v) of the X-ray image 40 after the image processing shown in FIG. 12A and FIG. 12B is denoted as A(u, v). For instance, by subtracting the pixel value I(u, v) of the DRR image 50 shown in FIG. 11A from the pixel value X(u, v) of the X-ray image 40 before the image processing shown in FIG. 10A, the pixel value A(u, v) of the X-ray image 40 after the image processing shown in FIG. 12A is generated.

Further, as one aspect of the image processing technique, inpainting processing as image processing can be applied to the X-ray image 40 shown in FIG. 10A. By performing this inpainting processing, the X-ray image 40 shown in FIG. 12A is generated. The region to be subjected to the inpainting processing is a part of the specific region Q where the pixels corresponding to the second region 42 of the fixture 9 are gathered. This specific region Q can be determined on the basis of the three-dimensional model information of the above-described extraneous regions such as the fixture 9 (i.e., non-index regions).

In this context, the X-ray image 40 includes detailed information on the shape of the skull S of the patient P. This detailed information includes information such as the irregularities (i.e., unevenness or convexoconcave) of the surface of the skull S and/or the detailed structure inside the skull S. In the above-described inpainting processing, such detailed information may be erased in some cases.

For this reason, a description will be given of one aspect of image processing in which detailed information is left with respect to the pixel value A(u, v) of the X-ray image 40 shown in FIG. 12A. Although the actual X-ray image 40 includes the detailed information, in order to aid understanding, it is assumed in the following description that the X-ray image 40 shown in FIG. 12A does not include the detailed information.

Figure 13A:
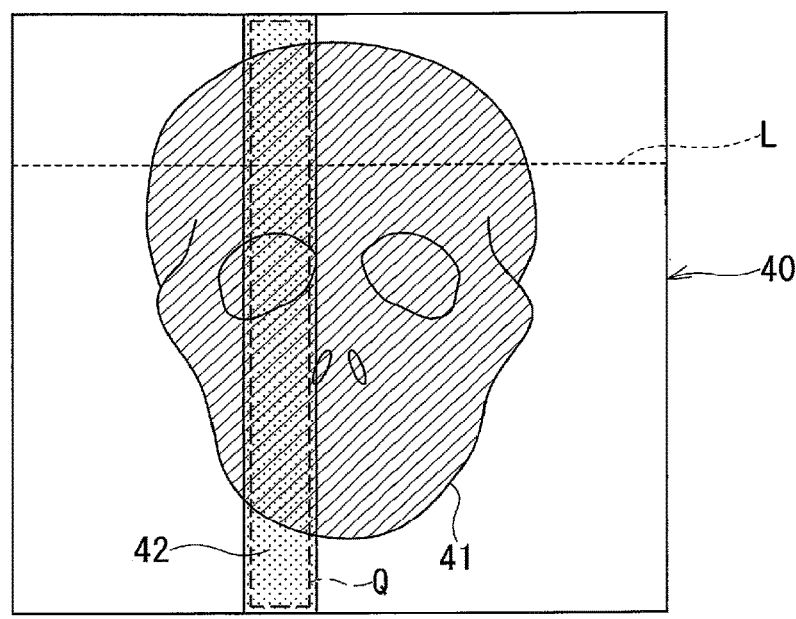
FIG. 13A to FIG. 13C are schematic diagrams illustrating the image processing technique according to the modification following FIG. 12B.

FIG. 13A is an X-ray image 40 before the image processing. In this X-ray image 40, the first region 41 of the skull S of the patient P and the second region 42 of the fixture 9 are included. Although the specific region Q is a region superimposed on the second region 42, the broken-line region indicative of the specific region Q is intentionally slightly shifted from the solid-line region indicative of the second region 42 in FIG. 13A in order to clearly distinguish between both. In the graph of the pixel value X(u, v) of the X-ray image 40 before the image processing in FIG. 13B, the horizontal axis indicates the position on the line L of the X-ray image 40 (i.e., u-axis) and the vertical axis indicates the luminance value (i.e., brightness) of each pixel corresponding to the line L of the X-ray image 40. In the X-ray image 40, the luminance value 44 of each pixel of the region where the first region 41 and the second region 42 are superimposed on each other includes the detailed information 45 indicative of the unevenness on the surface of the skull S or the detailed structure inside the skull S.

Figure 13B:
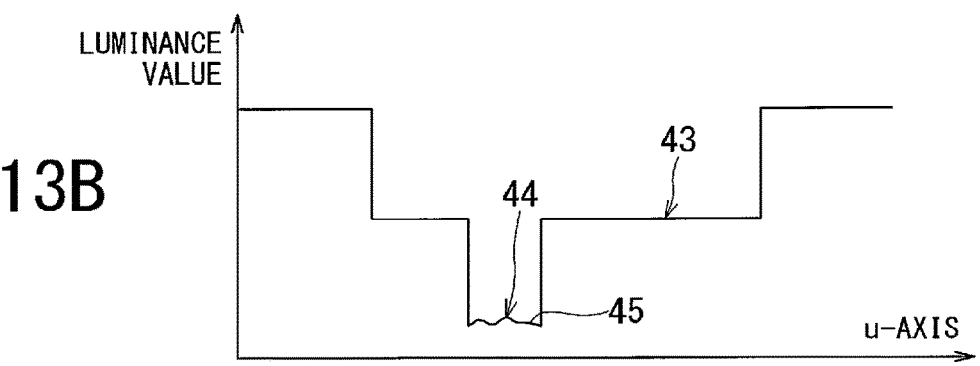
Figure 13C:
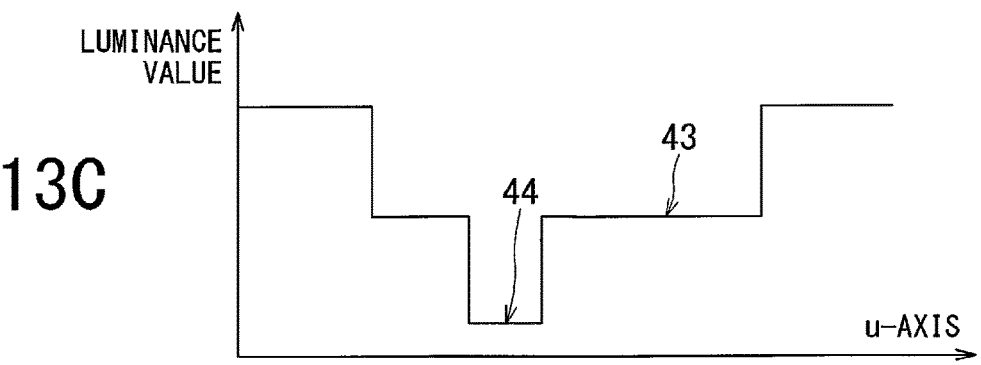

FIG. 13C is a graph of the pixel value Y(u, v) for subtraction. This graph includes the luminance value 43 of each pixel of the first region 41 and the luminance value 44 of each pixel of the region where the first region 41 and the second region 42 are superimposed on each other. On the basis of the DRR image 50 generated by the DRR image generator 20, it is possible to previously calculate the luminance value 43 of the first region 41 and the luminance value 44 of the region where the first region 41 and the second region 42 are superimposed on each other.

Figure 14A:
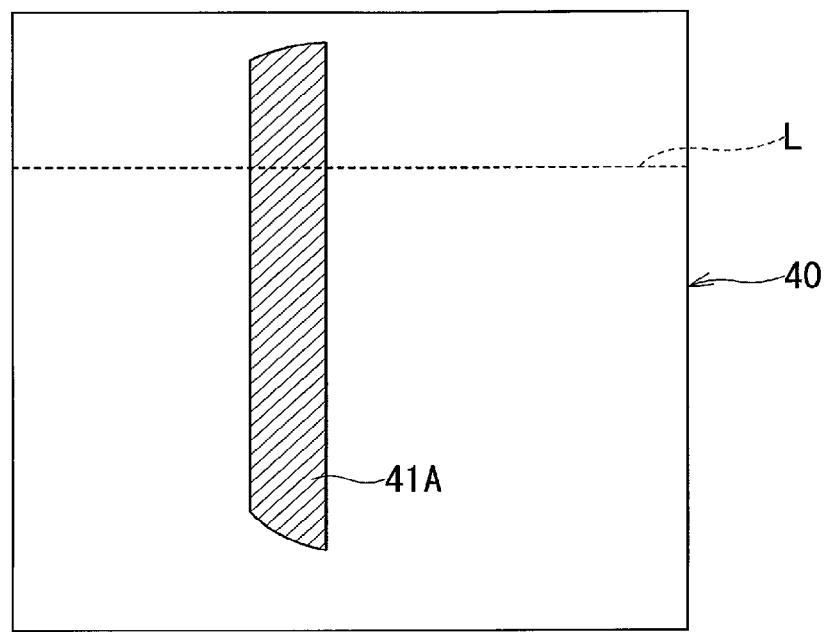
FIG. 14A and FIG. 14B are schematic diagrams illustrating the image processing technique according to the modification following FIG. 13C.
Figure 14B:
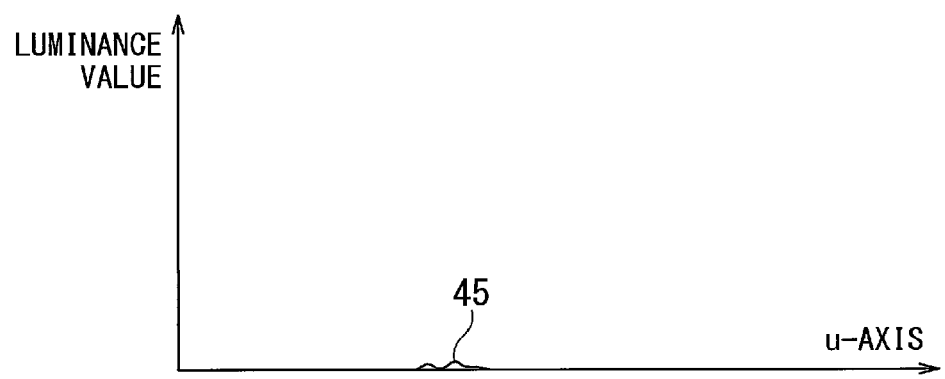

By subtracting the respective pixel values Y(u, v) shown in FIG. 13C for subtraction from the respective pixel values X(u, v) of the X-ray image 40 before the image processing shown in FIG. 13B, the graph of the subtracted pixel values T(u, v) can be obtained as shown in FIG. 14B. Note that FIG. 14A is the X-ray image 40 of the pixel values T(u, v) after the above-described subtraction. This X-ray image 40 includes a part 41A of the first region 41, i.e., includes the region where the first region 41 is superimposed on the second region 42 (FIG. 13A). Further, in the X-ray image 40 subjected to the subtraction as shown in FIG. 14A, only a part of the first region 41 remains such that the remained part of the first region 41 includes the detailed information 45.

Although a description has been given of the case where the pixel values Y(u, v) for subtraction are generated on the basis of the DRR image 50 generated by the DRR image generator 20 in the above-described aspect, embodiments of the present invention are not limited to such an aspect. For instance, in the case of estimating the pixel values T(u, v) shown in FIG. 14B, smoothing processing of edge-preserving type is performed with reference to the specific region Q in the X-ray image 40, and the pixel values Y(u, v) for subtraction in FIG. 13C are estimated. Further, it is preferable to estimate the pixel values T(u, v) after subtraction in FIG. 14B by subtracting the respective pixel values Y(u, v) in FIG. 13C from the respective pixel values X(u, v) in FIG. 13B. As the smoothing processing of edge-preserving type, e.g., a joint bilateral filter and/or a guided filter can be used.

Figure 15A:
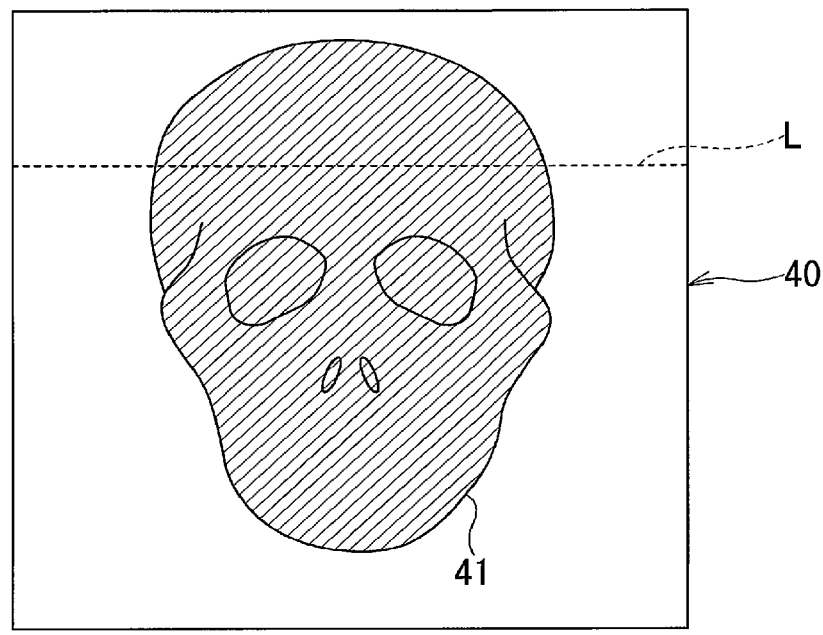
FIG. 15A and FIG. 15B are schematic diagrams illustrating the image processing technique according to the modification following FIG. 14B.
Figure 15B:
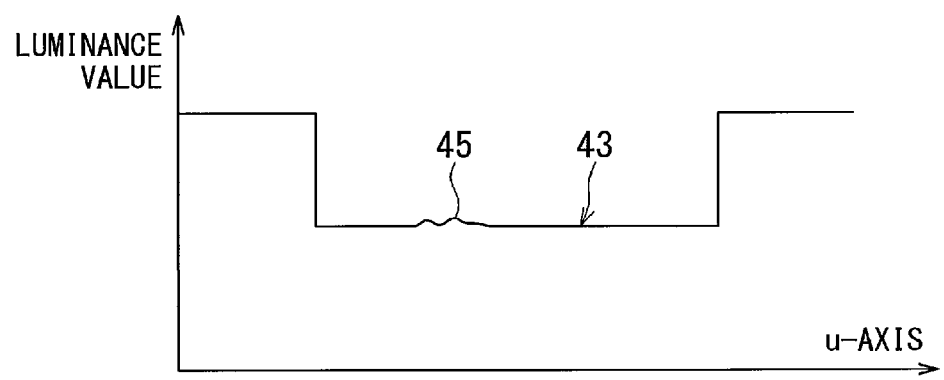

Further, by adding the respective pixel values T(u, v) in FIG. 14B to the respective pixel values A(u, v) in FIG. 12B, it is possible to generate the first region 41 that includes the detailed information 45 as shown in FIG. 15A. As shown in FIG. 15B, it is possible to generate the pixel values A(u, v) of the X-ray image 40 that includes the detailed information 45.

Although the image processing of performing the in-painting processing on the X-ray image 40 is exemplified, image processing without using the in-painting processing may be performed. For instance, when an error indicative of the similarity index value (i.e., gap amount of the position of the patient P) is defined as "e", this error e is calculated by using the following equation (3).

$$e = \sum_u \sum_v (I(u, v) - A(u, v))^2 \qquad \text{Equation (3)}$$

Here, A(u, v) indicates a virtual pixel value under the assumption that extraneous components being hard to transmit X-rays such as the fixture 9 (i.e., non-index region) do not exist in the imaging region of the X-ray imaging apparatus 3 and more X-rays reach from the X-ray irradiators 10 to the X-ray detectors 11. Additionally, X(u, v) is a known pixel value based on the actually generated X-ray image 40. In other words, in the case of generating the X-ray image 40 of the pixel values A(u, v) that are obtained by virtually eliminating the second region(s) 42 of the fixture 9 from the X-ray image 40, it is necessary to estimate the pixel values I(u, v) of the respective pixels of the second region 42 which depicts the fixture 9.

In the case of estimating the pixel values I(u, v), first, the DRR image 50 in which the second region 42 of the fixture 9 appears is generated on the basis of the three-dimensional volume image acquired at the time of treatment planning. The pixel value of this DRR image 50 is denoted as D(u, v). For instance, the pixel values I(u, v) are acquired by expressing the pixel values I(u, v) by linear transformation of the pixel values D(u, v) and estimating the coefficient. Although this estimation has an ill-posed problem, it can be solved by assuming that the coefficient is locally constant. By obtaining the pixel values I(u, v) in this manner, the pixel values A(u, v) are generated.

The positioning apparatus 4 may perform machine learning so as to generate an image in which every second region 42 is virtually removed from the X-ray image 40 including the first region 41 and the second region 42. In addition, the positioning apparatus 4 may perform machine learning for acquiring a function of outputting an image in which each pixel has the pixel value I(u, v). For instance, deep Learning and/or SVM can be used for machine learning. Further, an X-ray image 40 including the first region 41 and the second region(s) 42 may be inputted to a predetermined image processing apparatus that has performed machine learning. This is so that an X-ray image 40 in which every second region 42 is virtually removed is generated. Additionally, an X-ray image 40 including the first and second regions 41 and 42 and the DRR image 50 including the second region(s) 42 may be inputted to a predetermined image processing apparatus, so that an X-ray image 40 in which every second regions 42 is virtually removed may be generated.

When positioning of the patient P is performed, the following equation (4) may be used for calculating the error e indicative of the similarity index value (i.e., gap amount of the position of the patient P) between the DRR image 50 (i.e., reference image) and the X-ray image 40 (i.e., radiographic image). Since the second regions 42 of the extraneous regions such as the fixture 9 (i.e., non-index regions) are removed from the X-ray image 40 in this case, this case differs from the above-described first embodiment in that it is unnecessary in this case to distinguish pixels used for calculating the error e between the specific region Q and non-specific regions (i.e., all the regions except the specific region Q).

$$e = \sum_u \sum_v (I(u, v) - X(u, v))^2 \qquad \text{Equation (4)}$$

In this manner, it is possible to improve the matching accuracy between the first region 41 included in the X-ray image 40 and the reference region 51 of the DRR image 50, which facilitates positioning of the patient P.

Although the X-ray image 40 (i.e., radiographic image) is subjected to the image processing and then subjected to the matching processing with the DRR image 50 (i.e., reference image) in the present embodiment, the image processing on the X-ray image 40 before the matching processing may be omitted. In other words, the matching processing may be performed between the X-ray image 40 and the DRR image 50 from which the second region 42 is not removed. For instance, the generation of the DRR image 50 is performed in accordance with the actual arrangement of the respective components of the radiation therapy system 1. Thus, among pixels constituting the DRR image 50, it is possible to generate pixels of a region (typically, the specific region Q) that includes the second region 42.

For instance, it is determined whether virtual lines K connecting the X-ray irradiator 10 with the respective detection elements (i.e., detection pixels) on the detection plane of the X-ray detector 11 (FIG. 3) intersects with an extraneous component such as the fixture 9 or not. According to this determination result, pixels of the specific region in the image are determined as pixels corresponding to the detection pixels, each of which is at the end of the virtual line K determined to intersect with an extraneous component. In the case of generating an X-ray image on the basis of the three-dimensional volume image, by accumulating all the CT values existing on the virtual lines K connecting the X-ray irradiator 10 with the respective detection pixels of the X-ray detector 11, the pixel value (luminance value) of each pixel of the X-ray image can be calculated and pixels of the specific region Q can be generated by threshold processing.

Furthermore, instead of binarizing, for instance, plural discretized discrete values such as three values may be used by increasing number of threshold values or the pixel values may be used as a continuous value.

When the movement of the mounting table 5 is repeated until the error in pixel value between the X-ray image 40 and the DRR image 50, from which the second region 42 is not removed, becomes equal to or less than the threshold value as a result of the matching processing between both images, the pixel values of the specific region Q are not used. For instance, when the pixel values of the specific region Q of the X-ray image 40 are binary (0 or 1), the pixel values of the specific region Q are not used for error calculation. Further, when the pixel values of the specific region Q of the X-ray image 40 are continuous values (0 to n), it is preferable to control the weight of each pixel value at the time of error calculation.

Here, each pixel position of the DRR image 50 and the X-ray image 40 is denoted as (u, v), the pixel value at the pixel position of the DRR image 50 is denoted as I(u, v), the pixel value at the pixel position of the X-ray image 40 is denoted as X(u, v), a correction value for correcting each pixel value in the specific region Q or each pixel value in a region except the specific region Q is denoted as L(u, v), and an error indicative of the similarity index value (i.e., gap amount of the position of the patient P) between the DRR image 50 and the X-ray image 40 is denoted as e. Under this assumption, the error e is calculated by the following equation (5).

$$e = \sum_u \sum_v L(u, v)(I(u, v) - X(u, v))^2 \qquad \text{Equation (5)}$$

When the pixel value of the specific region Q is binary, the correction value for the specific region Q is set to L(u, v)=0 and the correction value for regions except the specific region Q is set to L(u, v)=1. In addition, when the pixel values of the specific region Q are continuous values, the correction value L(u, v) for the specific region Q is preferably brought close to zero and the correction value L(u, v) for regions except the specific region Q is preferably brought close to 1. It is preferable to repeat generation of the X-ray image 40 and movement of the mounting table 5 until the error e becomes equal to or less than the predetermined threshold.

In this manner, it is possible to perform positioning by performing the matching processing between the first region 41 of the X-ray image 40 and the reference region 51 of the DRR image 50 without performing image processing on the X-ray image 40. Although the error is the square error of the pixel value in the present embodiment, the error is not limited to the square error. For instance, a value representing an image difference such as an absolute value error or a normalized correlation may be used for the error.

Although two pairs of the X-ray irradiators 10 and the X-ray detectors 11 are provided in the present embodiment, X-ray images may be acquired from one or more directions by using one pair of the X-ray irradiator 10 and the X-ray detector 11 so as to be used for positioning of the patient P. Further, X-ray images may be acquired from three or more directions by using three or more pairs of the X-ray irradiators 10 and the X-ray detectors 1 so as to be used for positioning of the patient P.

In the present embodiment, the DRR image 50 generated at the time of treatment planning is set as the reference image and this DRR image 50 is subjected to the matching processing with the X-ray image 40 imaged during radiotherapy. However, an image other than the DRR image 50 may be used as the reference image. For instance, in the case of imaging the patient P to generate plural X-ray images 40 during radiotherapy, out of these plural X-ray images 40, the X-ray image 40 with earlier imaging time may be defined as the reference image and be subjected to the matching processing with the X-ray image 40 that is imaged after the reference image. In addition, when radiotherapy is performed plural times, the X-ray image 40 used for positioning at the first radiotherapy may be defined as the reference image and be subjected to the matching processing with the X-ray image 40 that is imaged at the time of the second radiotherapy. Even in these cases, by calculating each specific region from the X-ray image 40 and performing positioning, it is possible to perform positioning in which only the index region of the patient P is focused.

Second Embodiment

Next, a description will be given of the positioning apparatus 4A of the second embodiment to be used for positioning of an object by referring to FIG. 16 and FIG. 17. Note that the same reference signs are assigned to the same components as the above-described embodiment and modifications in each figure, and duplicate description is omitted. In addition, as to the configuration not specifically described below, the same configuration as described in the first embodiment can be applied without particular limitation.

Figure 16:
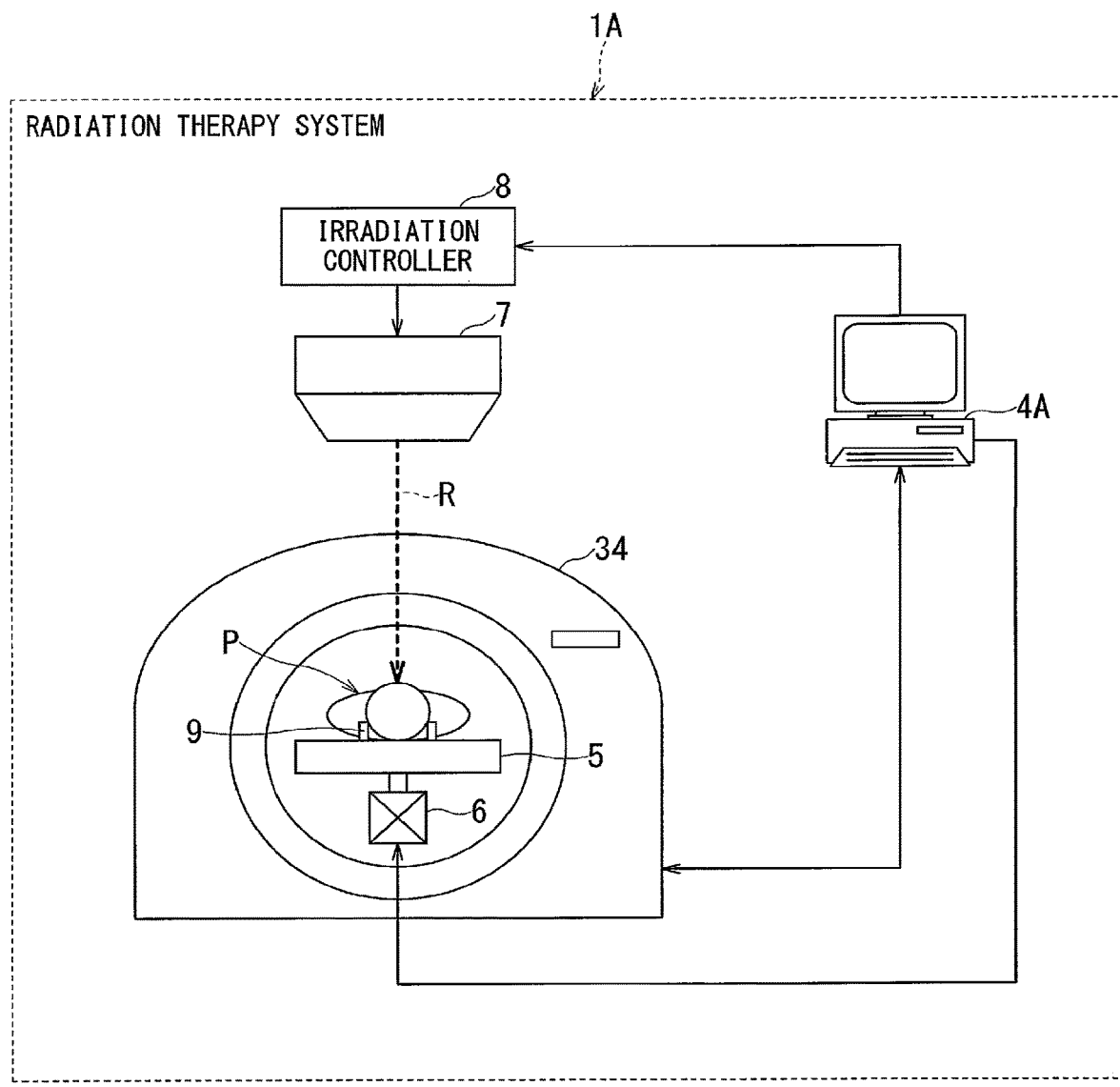
FIG. 16 is a configuration diagram illustrating the radiation therapy system according to the second embodiment.
Figure 17:
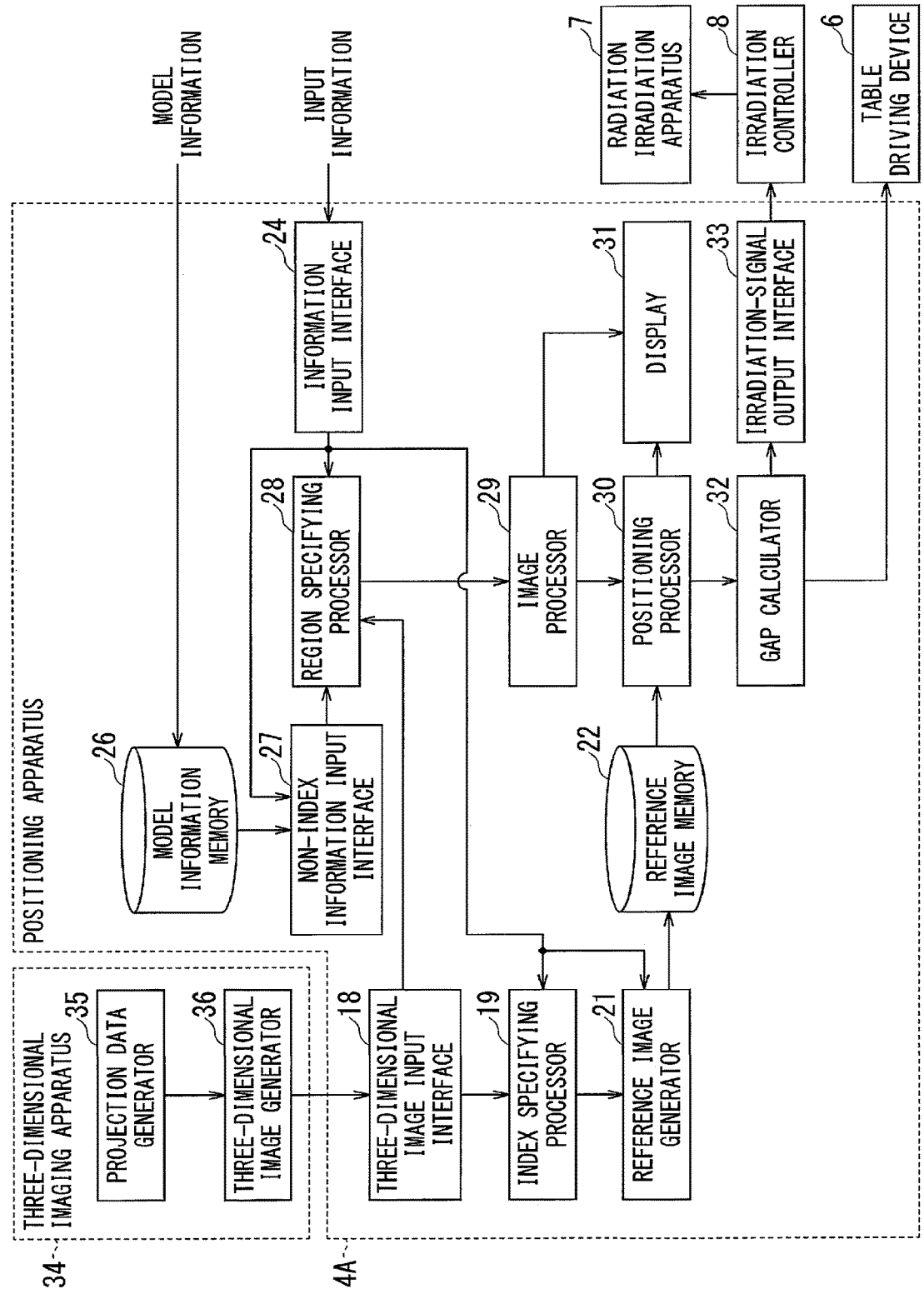
FIG. 17 is a block diagram illustrating the positioning apparatus according to the second embodiment.

As shown in FIG. 16, the radiation therapy system 1A according to the second embodiment includes a three-dimensional imaging apparatus (fluoroscopic imaging apparatus) 34 for generating three-dimensional volume images (fluoroscopic images) of the patient P, a positioning apparatus 4A configured to perform positioning of the patient P on the basis of this three-dimensional volume image, the mounting table 5, the table driving device 6, the radiation irradiation apparatus 7, and the irradiation controller 8.

Further, the three-dimensional imaging apparatus 34 includes a projection data generator 35 configured to generate projection data (fluoroscopic image data) from plural directions of the patient P and a three-dimensional image generator configured to generate a three-dimensional volume image in three dimensions of the patient P on the basis of the plural two-dimensional projection data acquired by the projection data generator 35.

The three-dimensional imaging apparatus 34 of the second embodiment is an X-ray CT apparatus having substantially the same configuration as the medical examination apparatus 2 of the first embodiment described above. In other words, at the time of planning a treatment plan, it is possible to perform computed tomography of the patient (object) P by using the three-dimensional imaging apparatus 34 of the radiation therapy system LA. It should be noted that the three-dimensional imaging apparatus 34 may be an MRI apparatus or an ultrasonic diagnostic apparatus.

In addition, the positioning apparatus 4A is connected to the three-dimensional imaging apparatus 34, the table driving device 6, and the irradiation controller 8. In the second embodiment, the reference image is generated on the basis of the three-dimensional volume image that is generated by causing the three-dimensional imaging apparatus 34 to image the patient P at the time of treatment planning.

For instance, the three-dimensional image input interface 18 of the positioning apparatus 4A acquires the three-dimensional volume image from the three-dimensional imaging apparatus 34. Further, the index specifying processor 19 specifies the region of the bone S (i.e., index region) of the patient P by analyzing the CT values of the three-dimensional volume image. Furthermore, the reference image generator 21 generates an index image on the basis of the specified region of the bone S. Thereafter, the reference image (i.e., three-dimensional volume image) including this index image is stored in the reference image memory 22.

In the second embodiment, the three-dimensional model information of extraneous regions (i.e., non-index regions) such as the mounting table 5 and the fixture 9 is inputted from the outside. The three-dimensional model information of the non-index regions is stored in the model information memory 26. In addition, the index specifying processor 19 may specify the non-index regions such as the mounting table 5 and the fixture 9 on the basis of various information items inputted to the information input interface 24 so as to remove the specified non-index regions from the three-dimensional volume image. In this manner, the reference image is generated from the three-dimensional volume image.

In the second embodiment, when positioning of the patient P is performed at the time of radiotherapy, the patient P is imaged by using the three-dimensional imaging apparatus 34 to generate the three-dimensional volume image (radiographic image) of the patient P, and then the three-dimensional image input interface 18 acquires the generated three-dimensional volume image. The acquired three-dimensional volume image is transmitted to the region specifying processor 28. Thereafter, the region specifying processor 28 extracts or specifies the second regions (i.e., non-index regions) such as the region of the fixture 9 included in the three-dimensional volume image, on the basis of the three-dimensional model information of the non-index region (s) stored in the model information memory 26. In the image processor 29, image processing for removing the second region such as the fixture 9 in the three-dimensional volume image is performed. As to the image processing method for removing the second region in the second embodiment, the methods described in the first embodiment can be applied without particular limitation.

Further, the positioning processor 30 performs the positioning of the patient P by performing the matching processing between the first region of the bone S of the three-dimensional volume image (radiographic image) imaged at the time of radiotherapy and the index image of the three-dimensional volume image (i.e., reference image) imaged at the time of treatment planning. In this manner, since the matching processing is performed between three-dimensional volume images, three-dimensional alignment of the region of the bone S (i.e., index region) is facilitated.

Although the three-dimensional model information of the non-index region(s) is externally inputted in the second embodiment, the three-dimensional model information may be acquired in other aspects. For instance, the three-dimensional model information of the non-index region(s) may be generated on the basis of the three-dimensional volume image imaged at the time of treatment planning in the second embodiment, in a manner similar to the first embodiment.

Although the object positioning apparatuses according to embodiments of the present invention have been described on the basis of the first and second embodiments, the configuration applied in any one of the embodiments may be applied to another embodiment and the configurations applied in the respective embodiments may be used in combination.

In the present embodiment, the determination of one value (i.e., gap amount) using a reference value (i.e., threshold value) may be determination of whether the target value is equal to or larger than the reference value or not.

Additionally or alternatively, the determination of the target value using the reference value may be determination of whether the target value exceeds the reference value or not.

Additionally or alternatively, the determination of the target value using the reference value may be determination of whether the target value is equal to or smaller than the reference value or not.

Additionally or alternatively, the determination of the one value using the reference value may be determination of whether the target value is smaller than the reference value or not.

Additionally or alternatively, the reference value is not necessarily fixed and the reference value may be changed. Thus, a predetermined range of values may be used instead of the reference value, and the determination of the target value may be determination of whether the target value is within the predetermined range or not.

In addition, an error occurring in the apparatus may be analyzed in advance, and a predetermined range including the error range centered on the reference value may be used for determination.

The positioning apparatus 4 of the present embodiment includes a storage device such as a ROM (Read Only Memory) and a RAM (Random Access Memory), an external storage device such as a HDD (Hard Disk Drive) and an SSD (Solid State Drive), a display device such as a display, an input device such as a mouse and a keyboard, a communication interface, and a control device which has a highly integrated processor such as a special-purpose chip, an FPGA (Field Programmable Gate Array), a GPU (Graphics Processing Unit), and a CPU (Central Processing Unit). The positioning apparatus 4 can be achieved by hardware configuration with the use of a normal computer.

Note that each program executed in the positioning apparatus 4 of the present embodiment is provided by being incorporated in a memory such as a ROM in advance. Additionally or alternatively, each program may be provided by being stored as a file of installable or executable format in a non-transitory computer-readable storage medium such as a CD-ROM, a CD-R, a memory card, a DVD, and a flexible disk (FD).

In addition, each program executed in the positioning apparatus 4 may be stored on a computer connected to a network such as the Internet and be provided by being downloaded via a network. Further, the positioning apparatus 4 can also be configured by interconnecting and combining separate modules, which independently exhibit respective functions of the components, via a network or a dedicated line.

Although the patient P that is a human being is exemplified as an object in the above-described embodiments, the positioning apparatus 4 may be used when an animal such as a dog and a cat is used as an object and radiotherapy is performed on the animal.

Although the positioning apparatus 4 of the above-described embodiments includes the display (i.e., monitor) 31 for displaying the X-ray images 40 and the DRR images 50, the configuration of the display 31 may be omitted.

Although the region of the bone S of the patient P is treated as the index region in the above-described embodiments, a region other than the bone S, e.g., the lesion area G may be treated as the index region. In this case, the positioning of the patient P may be performed by setting the region of the bone S of the patient P as the non-index region.

In the above-described embodiments, the positioning of the patient P is performed by moving the mounting table 5 on which the patient P is placed. However, the positioning of the patient P may be performed by moving the radiation irradiation apparatus 7. For instance, the mounting table 5 is fixed and the radiation irradiation apparatus 7 is configured to be able to move. Additionally, in the virtual space, the position of the reference region 51 included in the DRR image 50 and the position of the radiation irradiation apparatus 7 are fixed. Under the above-described setting, when the reference region 51 is moved so as to match the first region 41 of the X-ray image 40 of the patient P in the virtual space, the position of the radiation irradiation apparatus 7 is arbitrarily determined.

According to the above-described embodiments, by providing the positioning processor configured to perform positioning of an object by performing the matching processing between the first region and the previously generated reference image, it is possible to improve matching accurately between a radiographic image and a reference image and thus the positioning of the object is facilitated.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An object positioning apparatus comprising:
a radiographic image input interface configured to acquire a radiographic image that is a two-dimensional X-ray image taken from one direction generated by causing a fluoroscopic imaging apparatus to image an object when positioning of the object is performed, the radiographic image including a first region, a second region, and a superimposed region in which the first region and the second region are superimposed, the first region depicting an index region for the positioning of the object, and the second region depicting a non-index region other than the index region;
a three-dimensional image input interface configured to acquire a three-dimensional volume image including an image of the object before the positioning of the object is performed;
a reconstructed image generator configured to generate, based on the three-dimensional volume image acquired by the three-dimensional image input interface, a two-dimensional Digitally Reconstructed Radiograph (DRR) image to serve as a reference image;
a region specifying processor configured to specify a specific region in which the second region and the superimposed region are depicted in the radiographic image, based on three-dimensional model information of the non-index region;
a positioning processor configured to perform the positioning of the object by performing matching processing between the reference image and the first region which is included in a non-specific region other than the specific region in the radiographic image, wherein the first region is distinguished from the specific region; and
an image processer configured to perform image processing in which each pixel value of the second region is reduced to become lower than each pixel value of the first region, so as to eliminate the second region and the superimposed region in the two-dimensional X-ray image.

2. The object positioning apparatus according to claim 1, wherein the three-dimensional model information includes at least one of information on the fluoroscopic imaging apparatus, information on a mounting table on which the object is placed, and information on a medical restraint for fixing the object.

3. The object positioning apparatus according to claim 1, further comprising:
a three-dimensional image input interface configured to acquire the three-dimensional volume image including an image of the object before the positioning of the object is performed;
an index specifying processor configured to specify the index region and the non-index region based on the three-dimensional volume image acquired by the three-dimensional image input interface; and
a reference image generator configured to generate the reference image based on the index region and the non-index region, both of which are specified by the index specifying processor.

4. An object positioning method comprising:

acquiring a radiographic image that is a two-dimensional X-ray image taken from one direction generated by causing a fluoroscopic imaging apparatus to image an object when positioning of the object is performed, the radiographic image including a first region, a second region, and a superimposed region in which the first region and the second region are superimposed, the first region depicting an index region for the positioning of the object, and the second region depicting a non-index region other than the index region;

specifying a specific region in which the second region and the superimposed region are depicted in the radiographic image, based on three-dimensional model information of the non-index region;

acquiring a three-dimensional volume image including an image of the object before the positioning of the object is performed;

generating, based on the three-dimensional volume image acquired by the three-dimensional image input interface, a two-dimensional Digitally Reconstructed Radiograph (DRR) image to serve as a reference image;

performing the positioning of the object by performing matching processing between the reference image and the first region which is included in a non-specific region other than the specific region in the radiographic image, wherein the first region is distinguished from the specific region; and performing image processing in which each pixel value of the second region is reduced to become lower than each pixel value of the first region, so as to eliminate the second region and the superimposed region in the two-dimensional X-ray image.

5. A non-transitory computer-readable medium storing an object positioning program that allows a computer to perform:

a radiographic image acquisition process of acquiring a radiographic image that is a two-dimensional X-ray image taken from one direction generated by causing a fluoroscopic imaging apparatus to image an object when positioning of the object is performed, the radiographic image including a first region, a second region, and a superimposed region in which the first region and the second region are superimposed, the first region depicting an index region for the positioning of the object, and the second region depicting a non-index region other than the index region;

a region specifying process of specifying a specific region in which the second region and the superimposed region are depicted in the radiographic image, based on three-dimensional model information of the non-index region;

a three-dimensional image acquisition process of acquiring a three-dimensional volume image including an image of the object before the positioning of the object is performed;

a reconstructed image generation process of generating, based on the three-dimensional volume image acquired by the three-dimensional image input interface, a two-dimensional Digitally Reconstructed Radiograph (DRR) image to serve as a reference image;

a positioning process of performing the positioning of the object by performing matching processing between the reference image and the first region which is included in a non-specific region other than the specific region in the radiographic image, wherein the first region is distinguished from the specific region; and an image process of performing image processing in which each pixel value of the second region is reduced to become lower than each pixel value of the first region so as to eliminate the second region in the two-dimensional X-ray image.

6. A radiation therapy system comprising:

the object positioning apparatus according to claim 1; and a radiation irradiation apparatus configured to radiate radioactive rays onto a target region of the object subjected to positioning.

7. The object positioning apparatus according to claim 1, further comprising:

a three-dimensional image input interface configured to acquire the three-dimensional volume image including an image of the object before the positioning of the object is performed; and a model information generator configured to generate three-dimensional model information of the non-index region based on the three-dimensional volume image acquired by the three-dimensional image input interface.

* * * * *